United States Patent [19]
Griffith

[11] Patent Number: 5,852,172
[45] Date of Patent: Dec. 22, 1998

[54] COLD TOLERANCES IN PLANTS

[75] Inventor: Marilyn Griffith, Waterloo, Canada

[73] Assignee: University of Waterloo, Ontario, Canada

[21] Appl. No.: 419,061

[22] Filed: Apr. 10, 1995

Related U.S. Application Data

[63] Continuation of Ser. No. 60,425, May 11, 1993, abandoned.

[30] Foreign Application Priority Data

Jun. 13, 1991 [GB] United Kingdom .................... 9112774
Dec. 13, 1991 [GB] United Kingdom .................... 9126485

[51] Int. Cl.$^6$ .......................... C07K 14/415; C12N 9/32; C12N 9/34; C12N 9/42
[52] U.S. Cl. .......................... 530/379; 530/350; 530/370; 530/372; 435/204; 435/205; 435/209
[58] Field of Search ..................................... 530/380, 324, 530/350, 370, 372, 379; 435/183, 200, 205, 206, 209

[56] References Cited

U.S. PATENT DOCUMENTS

| | | | |
|---|---|---|---|
| 5,168,064 | 12/1992 | Bennett et al. | 435/320.1 |
| 5,554,521 | 9/1996 | Suslow et al. | 435/172.3 |

FOREIGN PATENT DOCUMENTS

| | | | |
|---|---|---|---|
| 90/13571 | 11/1990 | WIPO | 530/350 |

OTHER PUBLICATIONS

Manners et al. (1973) *Phytochem.*, 12(3), "Some Properties of a β–1,3–Glucanase from Rye", pp. 547–553.
Ballance et al.(1978) *Phytochem.*, 17(9), "Partial Purification and Properties of an Endo–1,3–β–D–Glucanase from Germinated Rye", pp. 1539–1543.
Huong etal, (1991) *Plant. Mol. Biol.*, 16, 479–480.
Burke et al, (1976) *Ann. Rev. Plant. Physiol.*, 27, 507–528.
Griffith et al. (1992) Plant Physiol., 100(2), 593–596, in *Biol. Abst.*, 95(2), 1020, Ref. No. 21137.
Griffith et al. (1992) *Cryobiology*, 26(6), 718, Ref. No. 45.
Marentes et al. (1993) *Physiol. Plant.*, 87, 499–507.
Duman (1992) *Cryobiology.*, 26(6), 718, Ref No. 44.
Zhiu et al. (1991) *Mol. Gen. Gent.*, 226(1/2), 289–296.
Olien et al. (1986) *Crop. Sci.*, 26, 189–191.
Leah et al. (1991) *J. Biol. Chem.*, 266(3), 1564–1573.
"Anomaluous Behavior of Ice in Solutions of Ice–Binding Arabinoxylans," R.J. Williams, *Thermochimica Acta*, 212 (1992) pp. 105–113.

"Antifreeze Protein Product by Winter Rye Leaves," M. Griffith, P. Ala, D.S.C. Yang, W.C. Hon & B.A. Moffatt, *Plant Physiology*, vol. 99, No. 1, May 1992, Supplement, Rockville, MD, p. 126.
"Primary Changes in Winter Rye Leaves During Cold Acclimation," S. Pihakaski, M. Antikainen, *Biological Abstracts*, vol. 92, 1991, ref. 57717.
"Cold Induced Protein Synthesis in Winger Rye," S. Pihakaski, M. Antikainen, *Physiol Plant*, vol. 79, 1990, 2 part, p. A105.
"Changes in Electrophoretic Patterns of the Soluble Proteins of Winter Wheat (Titicum Aestivum Cultivar Cappelle–Desprez) and Rye (Secale Ceraele Cultivar Puma) Following Cold Acclimation and Dessication Stress," Y. Cloutier, *Biological Abstracts*, vol. 78, 1984, ref. 37192.
"Changes of Protein Patterns in Winter Rye (Secale Cereale) Following Cold Acclimation and Dessication Stress," Y. Cloutier, *Biological Abstracts*, vol. 78, 1984, ref. 46852.
"Molecular Cloning and Characterization of Cold–Regulated Genes in Barley," L. Cattivelli, D. Barteis, *Plant Physiology*, vol. 93, 1990, Rockville, MD, pp. 1504–1520.
"Synthesis of Freezing Tolerance Proteins in Leaves, Crown, and Roots during Cold Acclimation of Wheat," M. Perras, f. Sarhan, *Plant Physiology*, vol. 89, 1989, Rockville, MD, pp. 577–585.
"Biochemical and Molecular Characterization of Three Barley Seed Proteins with Antifungal Properties, " R. Leah, H. Tommerup, I. Svendsen, J. Mundy, *Journal of Ciological Chemistry*, vol. 266, No. 3, 25 Jan. 1991, Baltimore, MD, pp. 1564–1573.
"Changes in Protein Patterns and Translatble Messenger RNA Populations During Cold Acclimation of Alfalfa," S. Mohapatra, R. Poole, R. Dhindsa, *Chemical Abstracts*, vol. 107, 1987, Columbus, Ohio.
"Functional Implications of the Subcellular Localization of Ethylene–Induced Chitinase and β–1,3–Glucanase in Bean Leaves," F. Mauch, L. Staehelin, *The Plant Cell*, vol. 1, Apr. 1989, Rockville, MD, pp. 447–457.

*Primary Examiner*—Jon P. Weber
*Attorney, Agent, or Firm*—Bell Seltzer Intellectual Property Law Group of Alston & Bird LLP

[57] ABSTRACT

A plurality of polypeptides derived from intercellular spaces of plant cells having frost tolerance. Some of the polypeptides are ice nucleators for developing ice crystals in extracellular spaces of plant tissue, some of the polypeptides are antifreeze components which control ice crystal growth in extracellular spaces and some of the polypeptides are enzymes which adapt plant cell walls to function differently during formation of ice crystals in plant intercellular spaces.

6 Claims, 12 Drawing Sheets

FIG. 11.
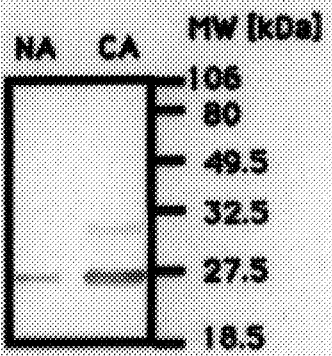
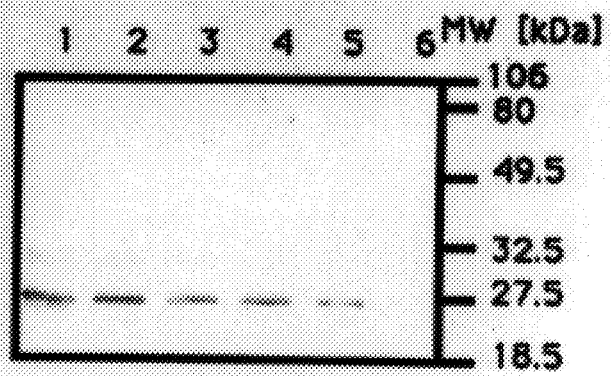
FIG. 12.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Secale cereale cv. Musketeer
        ( G ) CELL TYPE: Epidermal, mesophyl and vascular cells from leaves ( x i ) SEQUENCE DESCRIPTION: SEQ ID NO:1:

```
Ala  Ile  Phe  Cys  Gly  Gln  Val  Asn  Pro  Ala  Leu  Gly  Pro  Pro  Ile  Tyr
 1              5                        10                           15
Pro  Ala  Phe  Gly
          20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear (i i) MOLECULE TYPE: protein (i i i) HYPOTHETICAL: NO (i v) ANTI-SENSE: NO (v) FRAGMENT TYPE: N-terminal (v i) ORIGINAL SOURCE:
    (A) ORGANISM: Secale cereale cv. Musketeer
    (G) CELL TYPE: Epidermal, mesophyl and vascular cells from leaves (x i) SEQUENCE DESCRIPTION: SEQ ID NO:2:

```
Ala  Ile  Ser  Xaa  Gly  Glu  Gln  Val  Asn  Ser  Ala  Leu  Gly  Pro  Xaa  Ile
 1              5                        10                            15
Ser  Tyr  Ala  Arg  Gly
               20
```

(2) INFORMATION FOR SEQ ID NO:3:

(i) SEQUENCE CHARACTERISTICS:
    (A) LENGTH: 16 amino acids
    (B) TYPE: amino acid
    (C) STRANDEDNESS: single
    (D) TOPOLOGY: linear (i i) MOLECULE TYPE: protein (i i i) HYPOTHETICAL: NO (i v) ANTI-SENSE: NO (v) FRAGMENT TYPE: N-terminal (v i) ORIGINAL SOURCE:
    (A) ORGANISM: Secale cereale cv. Musketeer
    (G) CELL TYPE: Epidermal, mesophyl and vascular cells from leaves (x i) SEQUENCE DESCRIPTION: SEQ ID NO:3:

```
Arg  Ser  Phe  Ser  Ile  Thr  Asn  Arg  Cys  Trp  Ser  Phe  Thr  Val  Pro  Gly
 1              5                        10                            15
```

(2) INFORMATION FOR SEQ ID NO:4:

(i) SEQUENCE CHARACTERISTICS:
    (A) LENGTH: 25 amino acids
    (B) TYPE: amino acid
    (C) STRANDEDNESS: single
    (D) TOPOLOGY: linear (i i) MOLECULE TYPE: protein (i i i) HYPOTHETICAL: NO (i v) ANTI-SENSE: NO (v) FRAGMENT TYPE: N-terminal (v i) ORIGINAL SOURCE:
    (A) ORGANISM: Secale cereale cv. Musketeer
    (G) CELL TYPE: Epidermal, mesophyl and vascular cells from leaves (x i) SEQUENCE DESCRIPTION: SEQ ID NO:4:

```
Arg  Ser  Phe  Ser  Ile  Thr  Asn  Arg  Xaa  Ala  Phe  Thr  Val  Xaa  Pro  Ala
 1              5                        10                            15
Ala  Thr  Pro  Val  Gly  Gly  Gly  Gly  Gln
               20                        25
```

(2) INFORMATION FOR SEQ ID NO:5:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Secale cereale cv. Musketeer
        (G) CELL TYPE: Epidermal, mesophyl and vascular cells from leaves (xi) SEQUENCE DESCRIPTION: SEQ ID NO:5:

```
Ala  Thr  Ile  Thr  Val  Val  Asn  Lys  Phe  Ser  Tyr  Thr  Val  Xaa  Pro  Gly
 1              5                        10                            15

Ala  Leu  Pro  Phe  Gly  Gly  Val  Gly  Leu  Gly  Pro  Gly  Gln
              20                        25
```

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Secale cereale cv. Musketeer
        (G) CELL TYPE: Epidermal, mesophyl and vascular cells from leaves (xi) SEQUENCE DESCRIPTION: SEQ ID NO:6:

```
Ile  Gly  Val  Cys  Tyr  Gly  Val  Ile  Gly  Asn  Asn  Leu  Pro  Ser  Arg  Ser
 1              5                        10                            15

Asp  Val  Val  Gln  Leu  Tyr  Arg  Ser  Gly  Xaa  Ile  Asn  Xaa  Met
              20                        25                       30
```

(2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Secale cereale cv. Musketeer
        (G) CELL TYPE: Epidermal, mesophyl and vascular cells from leaves ( x i ) SEQUENCE DESCRIPTION: SEQ ID NO:7:

Glu Gln Xaa Gly Ser Gln Ala Gly Gly Ala Thr Xaa Pro Asn Asn Leu
 1               5                   10                  15

Leu ( 2 ) INFORMATION FOR SEQ ID NO:8:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Secale cereale cv. Musketeer
    ( G ) CELL TYPE: Epidermal, mesophyl and vascular cells from leaves ( x i ) SEQUENCE DESCRIPTION: SEQ ID NO: 8:

Ile Gly Val Xaa Tyr Gly Val Ile Gly Asn Asn Leu Pro Ser Arg Ser
 1               5                   10                  15

Asp Val Val Glu
          20

COLD TOLERANCES IN PLANTS

RELATED APPLICATION

This application is a continuation of U.S. application Ser. No. 08/060,425, filed May 11, 1993, now abandoned, for "Cold Tolerances in Plants" by Marilyn Griffith is a continuation-in-part of pending PCT International Application PCT/CA92/00255, filed Jun. 12, 1992, designating inter alia the United States.

FIELD OF THE INVENTION

The present invention relates to the identification and isolation of extracellular polypeptides which are associated with plant frost or cold tolerance and their use in mitigating the effects of frost and controlling crystalline growth of ice.

BACKGROUND OF THE INVENTION

In order to facilitate discussion of already known aspects of frost tolerance in plants and the contribution of the subject invention, several journal articles are referred to herein, in accordance with the following index numbers for the group I and group II listing of references.

GROUP I 1.0 Andersson J A, Ashworth E N (1986) The effects of streptomycin, desiccation and UV radiation on ice nucleation by *Pseudomonas viridiflava*. Plant Physiol 80: 956–960.

1.1 Cutler et al. (1989) J. Plant Physiology 135:351–354

2. Duman J G, Morris J P, Castellino F J (1984) Purification and composition of an ice nucleating protein from queens of the hornet, *Vespula maculata*. J Comp Biochem Physiol B 154: 79–83.

3.0 Fischer R, Behnke S, Apel K (1989) The effect of chemical stress on the polypeptide composition of the intercellular fluid of barley leaves. Planta 178: 61–68.

3.1 George et al. (1990) Gene 91:159–165

4. Guy C L (1990) Cold acclimation and freezing stress tolerance: role of protein metabolism. Annu Rev Plant Physiol Plant Mol Biol 41: 187–223.

5.0 Guy C L, Haskell D (1987) Induction of freezing tolerance in spinach is associated with the synthesis of cold acclimation-induced proteins. Plant Physiol 84: 872–878.

5.1 Guy C L, Neimi K J and Brambl R (1985) Altered gene expression during cold acclimation of spinach. Proc. Natl. Acad. Sci. USA 82:3673–3677.

5.2 Guy C L and Haskell D (1989) Preliminary characterization of high molecular mass proteins associated with cold acclimation in spinach. Plant Physiol. Biochem. 27:777–784.

6. Huner N P A, Macdowall F D H (1976) Chloroplastic proteins of wheat and rye grown at cold hardening temperatures. Can J Biochem 54: 848–853.

7. Kaku S (1973) High ice nucleating ability in plant leaves. Plant Cell Physiol 14: 1035–1038.

8. Kieft T L (1988) Ice nucleation activity in lichens. Appl Environ Microbiol 54: 1678–1681.

9.0 Kieft T L, Ruscetti T (1990) Characterization of biological ice nuclei from a lichen. J Bacteriol 172: 3519–3523.

9.1 Kurkela and Franck (1990) Plant Molecular Biology 15:137–144.

10. Laemmli U K (1970) Cleavage of structural proteins during the assembly of the head of bacteriophage T4. Nature 227: 680–685.

10.1 Legrand M, Kaufman S, Geoffroy P, and Fritig B (1987) Biological-Function of Pathogenesis-Related Proteins: Four Tobacco Pathogenesis-Related Proteins are Chitinases. Proc. Natl. Acd. Sci. USA 84:6750–6754

11. Lindow S E (1983) The role of bacterial ice nucleation in frost injury to plants. Annu Rev Phytopathol 21: 363–384.

12. Lindow S E, Arny D C, Upper C D, Barchet W R (1978a) The role of bacterial ice nuclei in frost injury to sensitive plants. In: Li P H, Sakai A (eds) Plant cold hardiness and freezing stress, vol I. Academic Press, London, New York, pp 249–263.

13. Lindow S E, Arny D C, Upper C D (1978b) *Erwinia herbicola*: A bacterial ice nucleus active in increasing frost injury. Phytopathology 68: 523–527.

14. Lindow S E, Arny D C, Upper C D (1982) Bacterial ice nucleation: A factor in frost injury to plants. Plant Physiol 70: 1084–1089.

15. Maki L R, Willoughby K J (1978) Bacteria as biogenic sources of freezing nuclei. J Appl Meteorol 17: 1049–1053.

16. Mauch F, Staehelin L A (1989) Functional implications of the subcellular localization of ethylene-induced chitinase and β-1,3-glucanase in bean leaves. Plant Cell 1: 447–457.

17. Meza-Basso L, Alberdi M, Raynal M, Ferro-Cardinanos M-L, Delseny M (1986) Changes in protein synthesis in rapeseed Brasica napus seedlings during a low temperature treatment. Plant Physiol 82: 733–738.

18. Mohapatra S S, Poole R J, Dhindsa R S (1987) Changes in protein patterns and translatable messenger RNA populations during cold acclimation of alfalfa. Plant Physiol 84: 1172–1176.

19. Mohapatra S S, Poole R J, Dhindsa R S (1988) Detection of two membrane polypeptides induced by abscisic acid and cold acclimation: possible role in freezing tolerance. Plant Cell Physiol 29: 727–730.

20. O'Farrell P H (1975) High resolution two dimensional electrophoresis of proteins. J Biol Chem 250: 4007–4021.

21. Perras M, Sarhan F (1989) Synthesis of freezing tolerance proteins in leaves, crown and roots during cold acclimation of wheat. Plant Physiol 89: 577–585.

22. Rajashekar C B, Li P H, Carter J V (1983) Frost injury and heterogeneous ice nucleation in leaves of tuber-bearing Solanum species. Plant Physiol 71: 749–755.

23. Robertson A J, Gusta L V, Reaney M J T, Ishikawa M (1987) Protein synthesis in bromegrass (*Bromus inermis* Leyss) cultured cells during the induction of frost tolerance by abscisic acid or low temperature. Plant Physiol 84: 1331–1336.

24. Southworth M W, Wolber P K, Warren G J (1988) Nonlinear relationship between concentration and activity of a bacterial ice nucleation protein. J Biol Chem 263: 15211–15216.

25. Warren G J (1987) Bacterial ice nucleation: molecular biology and applications. Biotechnol Genet Eng Rev 5: 109–135.

26. Wolber P, Warren G (1989) Bacterial ice nucleation proteins. Trends Biochem Sci 14: 179–182.

GROUP II 1.0 Abeles, F. B and Forrence L. E. (1970). Plant Physiology 45:395–400.

1.1 Ashworth, E. N. Plant Physiol. 92, 718–725 (1990).

2. Blum, A. CRC Crit. Rev. Plant Sci. 2, 199–238 (1985).

2.1 Broekaert W, Lee H, Kush A, Chua N H, Raikhel N (1990) Proceedings of the National Academy of Science IJSA 87: 7633–7637.

3. Chakrabartty, A., Yang, D. S. C. & Hew, C. L. J. Biol. Chem. 264, 11313–11316 (1989).
4. Davies, P. L. & Hew, C. L. FASEB J. 4, 2460–2468 (1990).
5. DeVries, A. L. Meth. Enzymol. 127, 293 (1986).
6. Duman, J. G., Xu, L., Neven, L. G., Tursman, D. & Wu, D. W. in Insects at Low Temperature, R. J. Lee, Jr. and D. L. Denlinger, Eds. (Chapman and Hall, New York, 1991), pp. 94–127.
7. Feeney, R. E. Comments Agric. & Food Chemistry 1, 147–181 (1988).
8.0 Fourney, R. M., Joshi, S. B. & Hew, C. L. Can. J. Zool. 62, 28–33 (1983).
8.1 Harlow, E. & Lane D. Antibodies, A Laboratory Manual. Cold Spring Harbor Laboratory, Cold Spring Harbor New York (1988).
8.2 Hejgaard J, Jacobsen S, Svendsen 1 (1991) FEBS Letters 291: 127–131.
8.3 Huang J K, Wen L, Swegle M, Tran H C, Thin T H, Naylor H M, Muthukrishnan S, Reeck G R (1991) Plant Molecular Biology 16: 479–480
9. Hew, C. L., Slaughter, D., Joshi, S. B., Fletcher, G. L. & Ananthanarayanan, V. S. J. Comp. Physiol. B 155, 81–88 (1984).
10. Knight, C. A. & Duman, J. G. Cryobiology 23, 256–262 (1986).
11. Krol, M., Griffith, M. & Huner, N. P. A. Can.J.Bot. 62, 1062–1068 (1984).
12. Mauch, F. & Staehelin, L. A. The Plant Cell 1, 447–457 (1989).
12.1 Neale A D, Wahleithner K A, Lund M, Bennett H T, Kelly A, Meeks-Wagner D R, Peacock W J, Dennis E S (1990) The Plant Cell 2: 673–684
13. Parody-Morreale, A., Murphy, K. P., Di Cera, E., Fall, R., DeVries, A. L. & Gill, S. J. Nature 333, 782–783.
14. Pearce, R. S. Planta 175, 313–324 (1988).
14.1 Pearson W R, Lipman D J (1988) Proceedings of the National Academy of Science USA 85: 2444–2448.
14.2 Molina A, Segura A, Garcia-Olmedo F, (1993) FEBS Lett. 316:119–122.
15. Sakai, A. & Larcher, W. Frost Survival of Plants (Springer-Verlag, Berlin, Heidelberg, 1987), pp. 1–38.
15.1 Schagger H, von Jagow G (1987) Analytical Biochemistry 166: 368–379.
16. Storey, K. B. & Storey, J. M. Physiol. Rev. 68, 27–84 (1988).
17. Tomchaney, A. P., Morris, J. P., Kang, S. H. & Duman, J. G. Biochemistry 21, 716–721 (1982).
18. Uemura, M. & Steponkus, P. Plant Physiol. 91, 1131–1137 (1989).
18.1 Wright C S, Raikhel N (1989) Journal of Molecular Evolution 28: 327336].
19. Wu, D. W., & Duman, J. G. J. Comp. Physiol. B 161, 279–283 (1991).
20. Wu, D. W., Duman, J. G. & Xu, Lei. Biochim. Biophys. Acta 1076, 416–420.

Low temperature is a major environmental limitation to the production of agricultural crops. For example, late spring frosts delay seed germination, early fall frosts decrease the quality and yield of harvests and winter low temperatures decrease the survival of overwintering crops, such as winter cereals and fruit trees. However, some plants have the ability to withstand prolonged subfreezing temperatures. If proteins involved in the development of frost tolerance in these plants, as well as the corresponding genes, can be identified, it may be possible to transform frost sensitive crop plants into frost tolerant crop plants and extend the range of crop production.

Biological organisms can survive icy environments by inhibiting internal ice formation. This strategy requires the synthesis of antifreeze proteins (AFPs) or thermal hysteresis proteins (THPs). Four distinct types of (AFPs) have been identified in fish (P. L. Davies & C. L. Hew. II-4) and a number of different THPs have been identified in insects. These previous findings suggest that this adaptive mechanism has arisen independently in different organisms. Antifreeze proteins are thought to bind to ice crystals to prevent further growth of the crystals. The presence of antifreeze proteins can be determined (1) by examining the shape of ice crystals as they form and (2) by measuring the existence of thermal hysteresis (the difference in temperature at which a particular solution melts and freezes).

It was generally understood that antifreeze proteins did not exist in plants. Instead, it was thought that some internal mechanism of the plant cells adapted them to withstand external ice crystal formation on their outer cell walls without damaging the cell. Kurkela and Franck (I-9.1) recently reported that a plant gene expressed at low temperature codes for a protein similar in amino acid sequence to the antifreeze protein of Davis et al (II-4). Kurkela et al, did not have sufficient amounts of the encoded protein to determine whether it exhibited an antifreeze activity in the plant and particularly within the plant cell. Cutler et al. (I-1.1) used fish antifreeze protein to demonstrate that the presence of antifreeze protein can increase frost tolerance in plants. George et al. (I-3.1) transformed corn protoplasts with a synthetic gene for the flounder antifreeze protein in an attempt to use antifreeze proteins for improving plant cold hardiness.

Guy et al. (I-5.1) discusses a rapid and stable change in the translatable poly(A)$^+$ RNA populations extracted from leaves of plants exposed to low temperatures. Total protein analysis of the plant tissues was conducted to detect proteins which might be associated with frost tolerance in plants. Proteins found in cold acclimated leaf extracts having molecular weights of 110 kd, 82 kD, 66 kD, 55 kD and 13 kD were not found in non-acclimated leaf extracts. It is thought that the increased expression of certain mRNAs may encode proteins that are involved directly in a development of increased freezing tolerance for the plant. Guy et al. (I-5.2) characterizes high molecular mass proteins which are believed to be associated with cold acclimation in spinach. As with Guy et al. (I-5.1) the total protein content of the acclimated spinach leaf is assessed. Cold acclimated proteins having molecular weights of 110 kD, 90 kD and 79 kD were identified. However, their location and function within the cell remain unknown.

SUMMARY OF THE INVENTION

It was the general impression that the mechanism responsible for frost tolerance resided within the cell so as to protect it internally from ice crystals which formed usually on the outside of the cell. No one had given any thought to the possibility of the existence of antifreeze proteins in plants and that, in addition to antifreeze proteins, ice nucleation proteins may also be present in the plant. Furthermore, no thought had been given to the possibility that such proteins could be located outside of the cell to effect an entirely different mechanism for protecting the plant from freezing. Quite surprisingly, we have found that a plurality of polypeptides occur extracellularly and provide for ice nucleation, antifreeze properties by controlling of ice crystal growth in the extracellular spaces and enzymatic activity, which adapts the plant cell wall to conform to the protoplast during formation of ice crystals, to retain plant cell viability upon plant thawing. These extracellular polypeptides are located in the extractable portion of the plant apoplast, which includes the outer surface of the plasmalemma, the region between the plasmalemma and the cell wall, the cell wall, the middle lamella, the intercellular spaces and the tracheids and vessels of the xylem. It is understood that throughout this specification, the term extracellular polypeptides has the above meaning.

According to an aspect of the invention, antifreeze polypeptides common to frost tolerant plants are provided. The polypeptides are located in the extracellular space to control ice crystal growth in the xylem and intercellular plant space, the control of ice crystal growth providing a degree of plant frost tolerance. The polypeptides associated with such antifreeze properties are selected from a group of polypeptides having respectively apparent molecular weights of about 5 to 9 kD, about 9 to 11 kD, about 11 to 15 kD, about 21 to 23 kD, about 24 to 27 kD, about 30 to 31 kD, about 31 to 33 kD, about 32 to 36 kD, about 60 and 68 kD, about 89 to 100 kD and about 161 kD.

According to another aspect of the invention, the plurality of polypeptides having the above molecular weights and derived from intercellular spaces of plant cells having frost tolerance is provided. Some of the polypeptides are ice nucleators for developing ice crystals in extracellular spaces of plant tissue, some of the polypeptides are antifreeze components which control ice crystal growth in extracellular spaces and some of the polypeptides are enzymes which adapt plant cell walls to function differently during formation of ice crystals in plant intercellular spaces.

According to another aspect of the invention, antibodies to one or more of the aforementioned polypeptides may be developed, such antibodies being optionally adapted for detection in an immunoassay for determining if a plant is frost tolerant.

According to another aspect of the invention, frozen food preparations may include one or more of the above polypeptides and in particular ice cream and fruit preparations which include one or more of the polypeptides to provide a superior product having minute crystalline structure. In addition, the polypeptides are useful in the cryopreservation of biological tissues, long term frozen storage of a variety of tissues and frozen germplasm storage.

According to various aspects of the invention, the polypeptides have been characterized by their apparent molecular weights based on their migration in SDS-PAGE gels relative to known molecular weight markers. It is appreciated that the polypeptides of this invention may migrate differently in different types of gels, particularly for different concentrations of acrylamide in the gel. Hence, the molecular weight characterization of the polypeptides of this invention is intended to cover the equivalent polypeptides as they might have slightly different molecular weights on different gels.

BRIEF DESCRIPTION OF THE DRAWINGS

Preferred embodiments of the invention shall be discussed with respect to the drawings wherein.

FIG. 11. Apoplastic extracts from nonacclimated (NA) and cold-acclimated (CA) winter rye leaves. Polypeptides were solubilized and separated by SDS-PAGE and then probed with anti-chitinase as the primary antibody. Molecular mass standards are in lane C (in kD).

FIG. 12. Western blot of apoplastic extract from cold-acclimated winter rye leaves. Polypeptides were separated by SDS-PAGE and blotted onto nitrocellulose. Blots were then probed with anti-chitinase as the primary antibody.

DETAILED DESCRIPTION OF THE PREFERRED EMBODIMENTS

Figure 1:
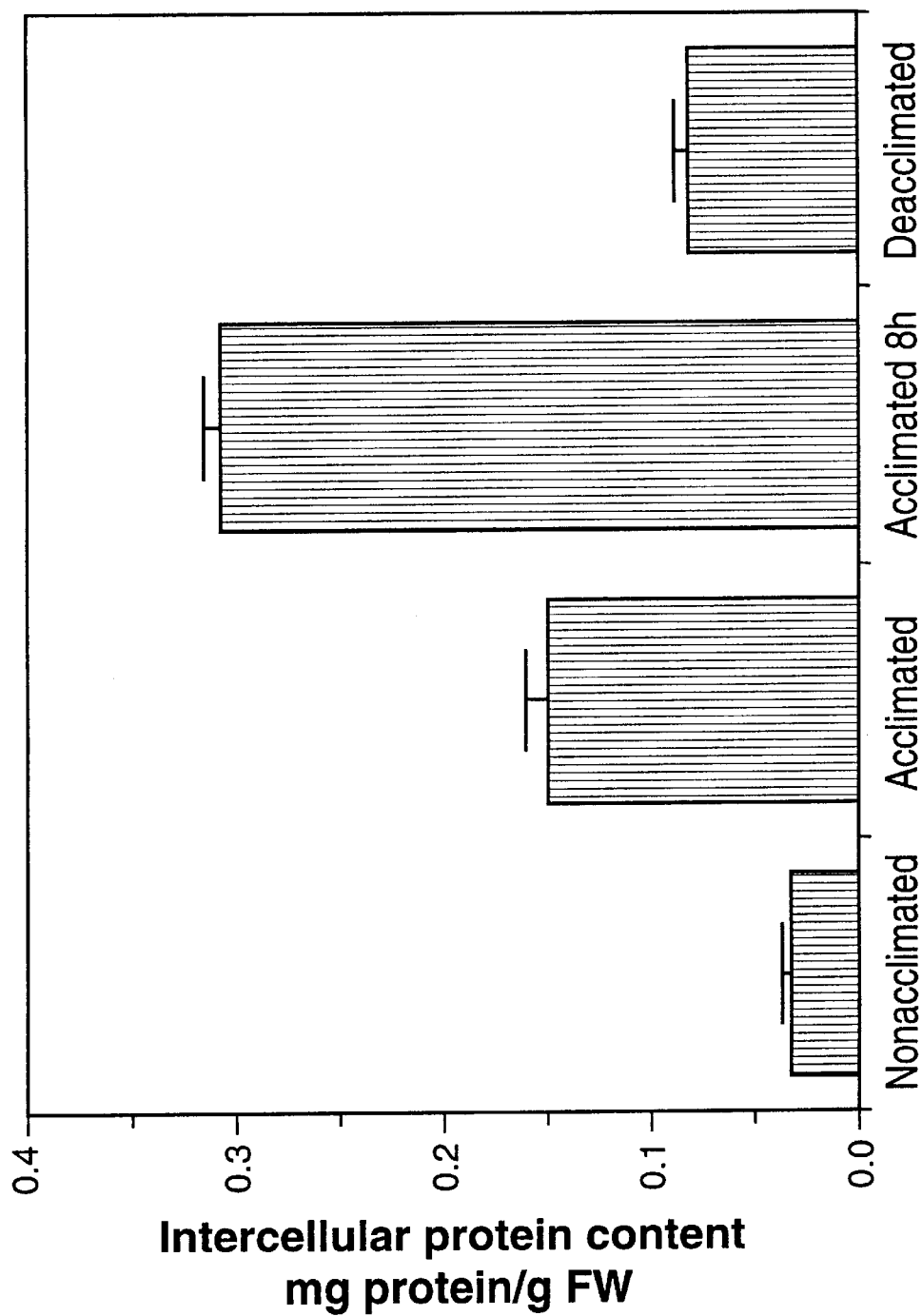
FIG. 1 depicts concentrations of proteins from the extracellular spaces of winter rye leaves grown under various temperature regimes.

The novel polypeptides which we have discovered and which are associated with plant frost tolerance are of 3 categories:

i) ice nucleation polypeptides, ii) ice crystal growth control polypeptides, and iii) polypeptides for enzymatic modification of cell wall.

The purpose of the ice nucleation proteins is to initiate ice crystal formation in the plant tissue when the plant tissue is exposed to freezing temperatures. By virtue of the ice nucleation proteins being located in the extracellular plant spaces, crystal growth is initiated in the intercellular spaces between the cell wall. The antifreeze proteins are also located outside the plasma membrane to control and limit crystalline growth in the intercellular spaces so as to not exert pressures on the cell membrane which would cause rupture thereof. The enzymes present in extracellular spaces function to increase the flexibility of the cell wall material to allow the cell wall to conform to the protoplast without damaging cellular material and retaining cell viability upon thawing of the plant tissue. In the process of freezing the water in the plant, tissue water is allowed to migrate through the cell walls into the intercellular spaces where the water is allowed to freeze under controlled conditions in forming the intercellular ice crystals.

It is believed that the proteins associated with frost tolerance are made endogenously by the plant cells and are secreted through the plasma membrane into the intercellular spaces to effect and modify ice crystal formation during freezing temperatures. It is understood that the make up of the frost tolerant proteins may comprise one or more of the identified polypeptides. More than one of the identified polypeptides may combine to provide a protein structure which provides one or more of the noted frost tolerant properties of ice nucleation, antifreeze or enzymatic action.

We have found that the polypeptides of the frost tolerant proteins are produced to a lesser extent by plant cells even at warmer temperatures such as 20° C. With the correct environmental conditions, production of the polypeptides associated with frost tolerance is dramatically increased as the plant is subjected to conditions which resemble early spring or late fall when frost can set in. To our knowledge this is the first finding of frost tolerance-inducing polypeptides being located in extracellular spaces of plant tissue. In view of our having located the subject polypeptides in intercellular spaces we extracted the polypeptides from those spaces (I-16 and II-12). Generally, the process is two-step and includes:

i) severed or cut leaves are vacuum infiltrated with an extraction buffer preferably containing 20 mM calcium chloride and 10 mM ascorbate, and ii) extracting the infiltrate from the plant tissue while the cells remain unbroken. The recovered extract exhibits ice nucleation activity, glucanase activity and chitinase activity as well as antifreeze activity.

Preferably ice nucleation activity can be measured by the droplet freezing assay. The ice nucleation activity decreases upon addition of sulfhydryl reducing agent such as dithiothreitol and mercaptoethanol in the manner to be discussed with respect to the examples. The antifreeze activity of the extract was determined by observing ice crystal formation on a freezing stage mounted on a light microscope. In the presence of the extract the ice crystals form bipyrimidal and hexagonal structures which indicate control in the crystalline growth. Such structures are similar to those formed in the presence of other types of antifreeze proteins isolated from other sources such as the sea raven fish (II-4). It has been found that the addition of protease to the extract eliminates the antifreeze activity which indicates the presence of a protein. The glucanase activity is measured as the enzymatic release of glucose equivalents from soluble laminaran (poly-beta-1,3-glucose). The glucanase is more active in the presence of calcium. Chitinase activity is measured as the enzymatic release of glucosamine from colloidal chitin (exochitinase) and from chitin oligomers (endochitinase) [I-10.1].

It is understood that various separation techniques may be employed which remove the infiltrate from the intercellular spaces without rupturing the plant cells. Such techniques include vertically orienting the leaves in a funnel placed inside a centrifuge tube. Such vertical layering avoids severe bending of the leaves. The leaves are then centrifuged to recover the infiltrate without rupturing the cells. Other techniques are available for polypeptide extraction. For example, leaves may also be extracted by perfusion with appropriate extraction solutions. The extracellular polypeptides are water-soluble and are found in the total soluble fraction when plant tissues are homogenized.

The frost tolerance inducing polypeptides are beneficial to any type of plant where intercellular ice formation can be initiated and ice crystal growth controlled. Any plant tissue can, in a variety of ways, be adapted to provide or include these polypeptides so that they can withstand lower freezing temperatures and hence, are more likely to survive harsher climates or provide at least prolonged growing periods in the later fall and earlier growth in the early spring. It has also been found that in some species of plants supercooling of the plant liquids may be achieved at temperatures below −35° C. It is possible that the antifreeze polypeptides are produced in the absence of any nucleating peptides. Such antifreeze peptides serve to supercool the plant liquids to permit survival of the cell.

As can be appreciated, the frost tolerant proteins as provided by this invention have a variety of uses. A significant use is in the detection of frost tolerant characteristics in plants. Antibodies may be developed to one or more of the polypeptides and by way of an immunoassay other plants can be tested for the presence of polypeptides to determine their frost tolerance capability. It is also understood that plants could be transformed with genetic information which encodes for the subject polypeptides to improve or provide frost tolerance in other types of plants. The polypeptides of this invention may also be applied to plant matter. Suitable carriers for the polypeptides may be used which expedite absorption of the polypeptides into the plant cells of leaves and fruit. In this manner, the polypeptides would be applied by spraying techniques to avoid frost damage to vegetable crops, fruit crops and the like when ambient temperatures drop suddenly below freezing temperature. Furthermore, the polypeptides would be useful in the cryopreservation of biological tissues. Polypeptides also have a broad application in improving the quality of frozen foods and in particular, ice cream and frozen fruit. The use of the polypeptides would induce minute crystalline structure in the ice and prevent recrystallization to produce a superior product. In principle, the polypeptides of this invention are useful whenever it is desired to inhibit recrystallization of ice particles. Such inhibition of recrystallization prevents damage to cell walls, maintains viability of stored tissue and promotes formation of fine ice crystals. The formation of fine ice crystals not only limits the damage done to the cell membrane, but as well enhances the quality of frozen food products.

Further aspects of the invention will be understood based on the following specific discussion and examplification of the invention.

EXPERIMENTAL PROTOCOL

Production of Plant Material

Winter rye seeds (*Secale cereale* L. cv. Musketeer) were sown in 15 cm plastic pots containing coarse vermiculite and germinated for one week at 20°:16° C. (day:night) with a 16 hour daylength. Plants transferred to a at 5°:2° C. (day:night) and a light regime of 16:8 h (day:night) are referred to as cold acclimated rye (RH). Plants grown at 5°:2° C. (day:night), but with a light regime of 8:16 h (day:night) are referred to as cold acclimated rye—short day (RH-SD). The pots that remained in the growth chamber at 20° C. for another three weeks are control or nonacclimated rye plants (RNH). Rye plants that were grown at 5°:2° C. (day:night) (8 h day:16 H night) for exactly seven weeks and then were shifted to the growth chamber at 20° C. for four days are referred as deacclimated (Deacc). All plants were watered with modified Hoagland nutrient solution as described by Huner and Macdowall (I-6).

Protein Extraction

Extracellular proteins were removed from the leaves of RNH, RH, RH-SD and Deacc plants. In each instance the extracellular extracts were prepared by vacuum infiltration of the leaves with 5 mm EDTA, 10 mm ascorbic acid, 10 mm mercaptoethanol, 1 mm phenylmethyl sulfonylfluoride, 2 mm caproic acid and 2 mm benzamidine. The vacuum infiltration is in accordance with the process described in Mauch and Staehelin (I-16). The treated leaves were packed vertically in a funnel placed in a centrifuge tube so as to avoid bending of the leaves. With the leaves packed in the funnel the material was centrifuged to remove without rupturing the cells of the leaves the extracellular infiltrate which is captured in the centrifuge tube as an extract.

Protein Electrophoresis

Figure 2:
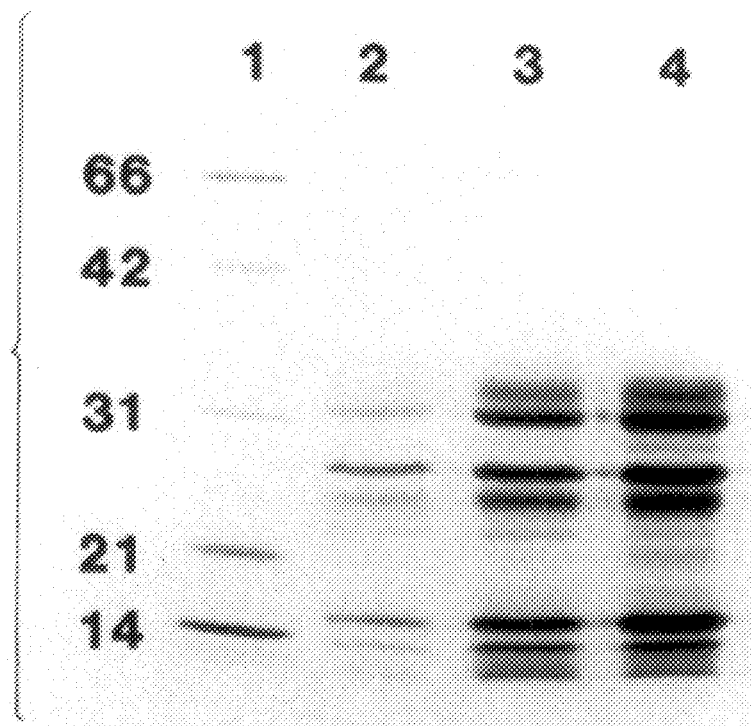
FIG. 2 depicts an SDS-PAGE of extracellular space proteins isolated from winter rye leaves grown under various temperature regimes where lane 1, molecular mass markers; lane 2, extracellular polypeptides from rye plants grown at 20°/16° C. (day/night) with a 16 hour day; lane 3, extracellular polypeptides from rye plants grown at 5°/2° C. with a 16 hour day; lane 4, extracellular polypeptides from rye plants grown at 5°/2° C. with an 8 hour day.
Figure 3:
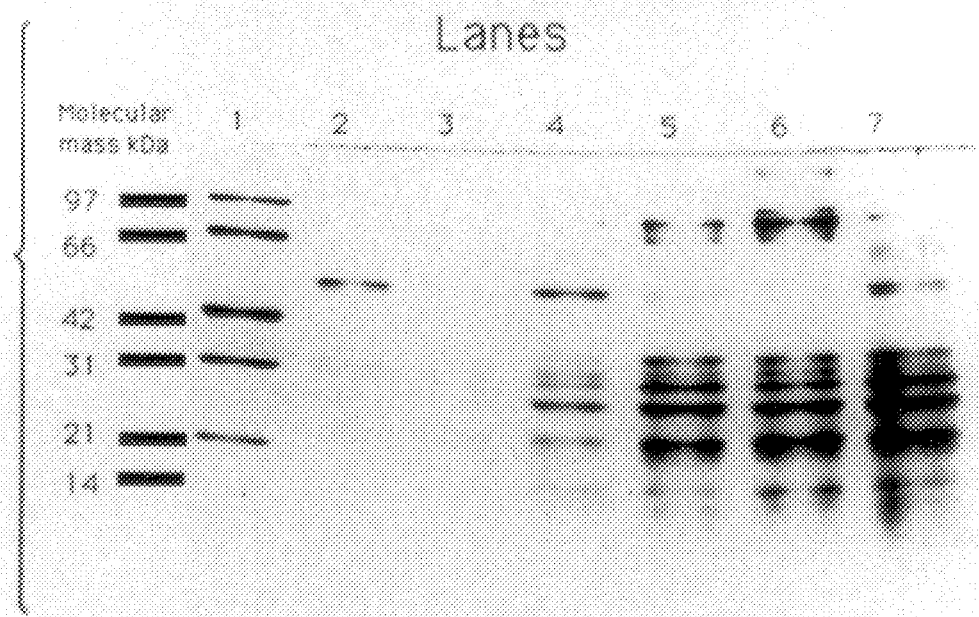
FIG. 3 depicts an SDS-PAGE of extracellular space polypeptides isolated from cold acclimated winter rye leaves grown with an 8-hour daylength at different stages of development where lane 1, molecular mass markers; lane 2, extracellular polypeptides from rye plants grown at 20°/16° C. with a 16 hour day for 7 days; lane 3, extracellular polypeptides from rye plants (20°/16° C., 7 days old) transferred to 5°/2° C. with an 8 hour day for 28 days; lane 4, extracellular polypeptides from rye plants transferred to 5°/2° C. for 43 days; lane 5, extracellular polypeptides from rye plants transferred to 5°/2° C. for 50 days; lane 6, extracellular polypeptides from rye plants transferred to 5°/2° C. for 71 days; lane 7, extracellular polypeptides from rye plants transferred to 5°/2° C. for 95 days.
Figure 4:
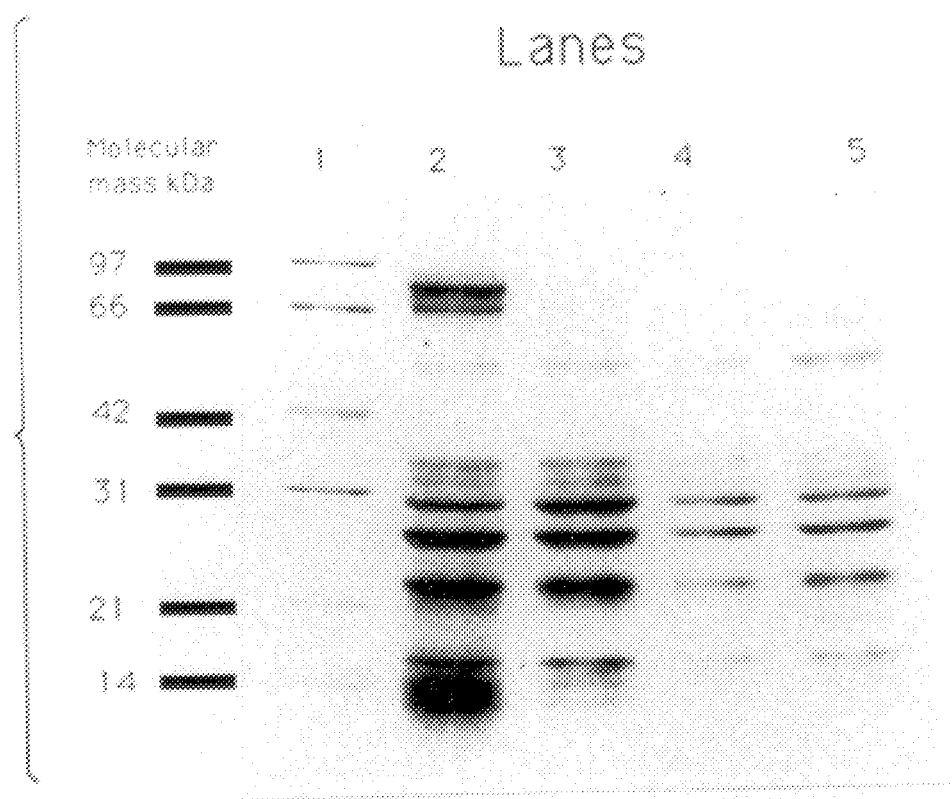
FIG. 4 depicts an SDS-PAGE of extracellular space proteins isolated from deacclimating winter rye leaves where lane 1, molecular mass markers; lane 2, extracellular polypeptides from plants grown at 20°/16° C. for 7 days and then transferred to 5°/2° C. with an 8 hour day for 42 days; lanes 3, 4 and 5, extracellular polypeptides from plants grown as described in lane 2 and then transferred to 20°/16° C. with an 16 hour day for 4, 6 and 8 days, respectively.

For the results presented in FIGS. 2, 3 and 4, the extracellular proteins were precipitated from extracellular extracts for purposes of electrophoresis by the addition of 1.5 volumes of 1% acidic acid in methanol and incubating overnight at −20° C. The protein pellet was washed with 100% ethanol and 70% ethanol at 5° C. and then dried in a desiccator. The protein was resuspended in Laemmli (I-10) sample buffer [60 mM Tris-HCl, pH 6.8; 10% glycerol; 2% sodium dodecyl sulfate (SDS); 5% mercaptoethanol] and separated by electrophoresis, along with Biorad unstained standards, on 10% acrylamide gels using 90 V for the stacking gel and 110 V for the separating gel (I-10). The gels were stained with Coomassie blue. For the results presented in FIG. 9, proteins present in column fractions of the extracellular extracts were solubilized directly in Laemmli sample buffer (I-10), separated by electrophoresis, along with Biorad prestained standards, on 13.5% acrylamide gels at 200 V. The gels stained with ammoniacal silver.

Quantification of Extracellular Proteins

Extracellular proteins were extracted from RNH, RH, RH-SD and Deacc rye leaves, as outlined above in "Protein Extraction". Protein concentration of the different extracts was determined by the Bio-Rad method with BSA as the standard. At least four replicates were run to obtain an accurate estimate of the extractable extracellular protein content in the different types of leaves. The extracellular extracts from leaves were subjected to ultrafiltration through an Amicon minicon membrane to concentrate the extracts approximately ten times and to remove compounds that interfered with INA assay (I-13). The protein concentration of all extracts after ultrafiltration was again determined by the Bio-Rad method. Concentrated extracts were used in the droplet freezing technique to determine the spectrum of active ice nuclei within a given temperature range.

Polypeptides extracted from the Extracellular space of rye leaves:

Different amounts of proteins can be extracted from the extracellular,,space by the various treatments. Nonacclimated leaves (hardy to −12° C.) had an extracellular protein content averaging 0.034 mg protein/g fresh weight. This amount of protein increased when leaves were allowed to develop at 5° C. with either a daylength of 16 hours (hardy to −19° C.), protein content of 0.149 mg/g fresh weight, or a daylength of 8 hours (hardy to −30° C.), protein content of 0.307 mg/g fresh weight. Thus there is a 9 fold increase in extracellular proteins in rye plants grown at 5° C. with a short daylength as compared with the protein levels in nonacclimated rye plants grown at 20° C. These protein levels decreased when the leaves were shifted back to 20° C. to acclimate (FIG. 1).

The protein profile of extracellular extracts shows remarkable changes between the different types of leaves. Using 10% acrylamide gels, the SDS-PAGE electrophoresis analysis of the intercellular fluid revealed the presence of at least 12 polypeptides. Two of these extracellular polypeptides with molecular masses of 77 and 73 kDa were observed in extracellular fluids from cold acclimated leaves only (FIG. 2; lanes 3 and 4). The 77 and 73 kDa polypeptides stained red with Coomassie blue. Increases of eight polypeptides with molecular masses of 36, 33, 30, 25, 21, 15, 14 and 13 kDa were observed in extracellular fluids from acclimated leaves (FIG. 2). Increases in two polypeptides with molecular masses of 23 and 20 kD were observed only in leaves cold-acclimated with a short day.

To further characterize the polypeptides of the intercellular spaces, a time course study was carried out with the aim of correlating the appearance of these polypeptides with the development of the freezing tolerance. Most of the polypeptides of the intercellular spaces were detected at very low levels in nonacclimated leaves (FIG. 3, lane 2). The polypeptides accumulated steadily during cold acclimation for 35, 50, 57 and 78 days (FIGS. 3, lanes 3, 4, 5 and 6). At 78 days, rye leaves cold acclimated with a short day are maximally frost tolerant, exhibit the highest levels of all extracellular polypeptides and exhibit a new polypeptide at 109 kD. After cold acclimation for 102 days, the 109, 77 and 73 kDa polypeptides were no longer present and the leaves are less frost tolerant (FIG. 3, lane 7). This finding suggests that the appearance of most of these 13 polypeptides in the extracellular space are correlated with changes in frost tolerance. The extracellular protein profile was also monitored during deacclimation by transferring cold acclimated plants at their hardiest stage to a 20° C. environment for different lengths of time. As shown in FIG. 4, the levels of most of the 12 intercellular polypeptides (lane 2, maximally cold-acclimated) were greatly reduced following 4 days of deacclimation (lane 3) and continued to decline steadily after deacclimation for 6 and 8 days (lanes 4,5). The molecular weight markers are in the left hand column which are understood to approximate the molecular weights of the polypeptides in lane 1. The column of molecular weight between lane 1 and lane 2 is believed to be more accurate.

Figure 5:
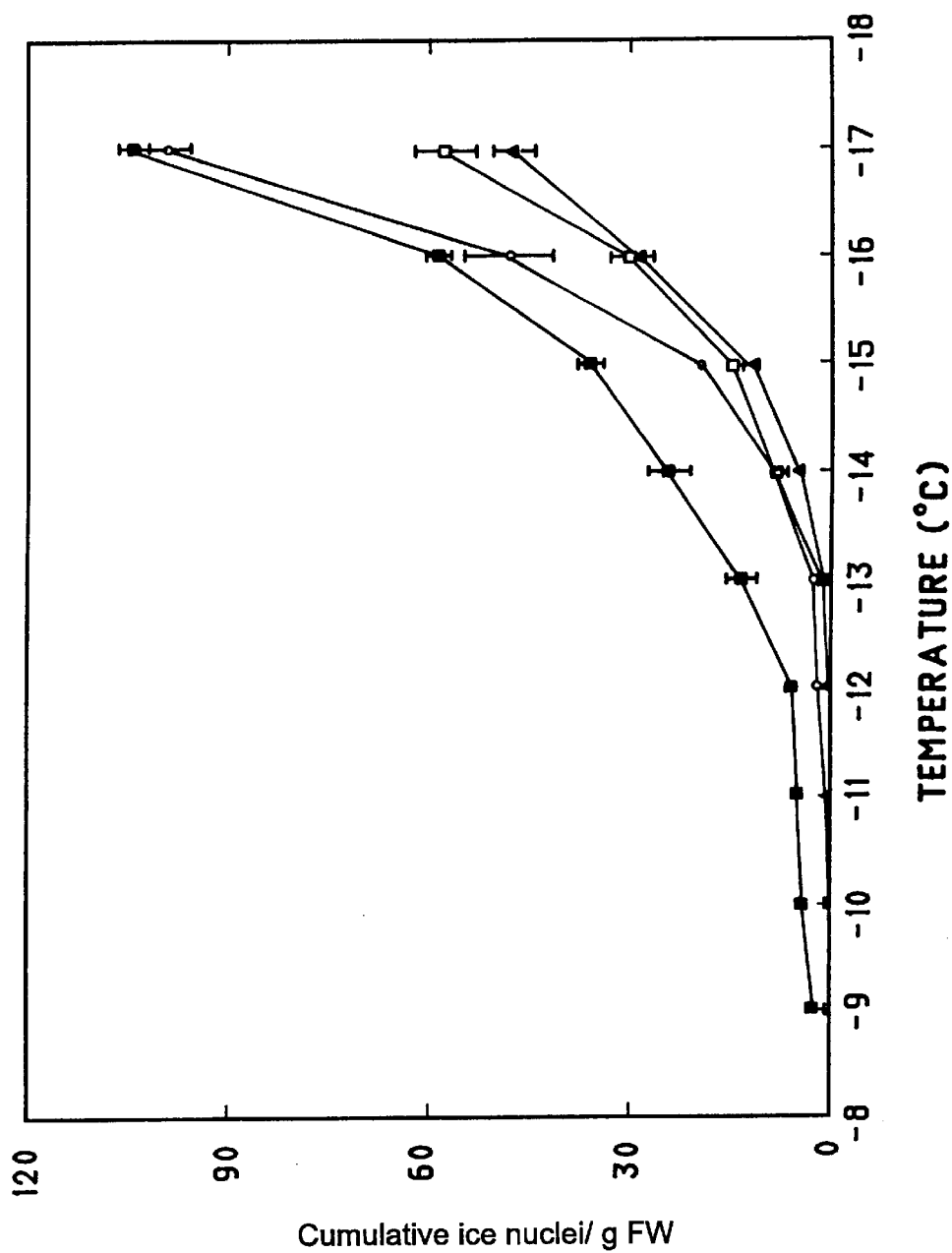
FIG. 5 depicts the ice nucleation activity of various ultrafiltered extracellular extracts from rye leaves grown under different temperature regimes.

To verify that the presence of these extracellular space polypeptides are essential to the induction of freezing tolerance and not merely a result of low-temperature exposure, freezing studies were carried out on the extracellular extracts from different types of leaves (FIG. 5). Extracellular extracts from cold acclimated rye leaves grown under a short photoperiod initiate ice formation at −9° C. (■), whereas extracts from cold-acclimated rye leaves grown under a long photoperiod initiate ice formation at −10° C. (○). The extracts from nonacclimated (□) and deacclimated leaves (Δ) initiate ice formation at the lowest temperature (−13° C.). The difference in ice nucleation activity of the extracellular extracts between nonacclimated and cold acclimated leaves (FIG. 5) may be attributed to the fact that acclimated leaves maintain higher levels of proteins in the extracellular spaces (FIG. 1). The effect of protein concentration was examined by using ultrafiltration to obtain nonacclimated and cold acclimated extracellular extracts that were equal in protein content. When ice nucleation activity was assayed and calculated for the two extracts, a striking increase in the cumulative number of ice nuclei per gram fresh weight was found in cold acclimated leaves. The number of ice nuclei per gram fresh weight (mean±standard deviation) at −15° C. was 2268.7±292.1 in intercellular extracts from nonacclimated leaves and 7047.6±916.6 in extracts from cold acclimated rye leaves grown under a long daylength. A statistically significant increase in the number of ice nuclei per gram fresh weight was found in the extracts of cold acclimated rye leaves between the two extracts as determined by a Student's t test ($\alpha=0.01$, n=4). The low threshold temperature for nucleation suggests that the ice nucleators present in the extracts are not intact ice nucleation sites.

Antifreeze Activity of Extracellular Proteins

Extracellular proteins as extracted in accordance with the above technique were evaluated with respect to antifreeze activity. The antifreeze activity was determined by observing ice crystal morphology using a nanoliter osmometer (Clifton Technical Physics, Hartford, N.Y., U.S.A.) and (II-3). Orientation of the ice crystals in FIGS. 6 C, D, E, F: the a-axis represents growth in the basal plane and the c-axis represents growth normal to the basal plane. (A) is an ice crystal formed in distilled water, oriented so that the c-axis is perpendicular to the plane of the paper. (B) is an ice crystal formed in presence of extracellular extract of non-acclimated plant. (C, D, E & F) are growth sequences of an ice crystal in the presence of crude extracellular extract from cold acclimated winter rye leaves as the temperature was lowered. (G) is a hexagonal column of ice as shown in (F) reoriented so that the c-axis is perpendicular to the plane of the paper.

Fractionation of proteins of extracellular extracts

Figure 7:
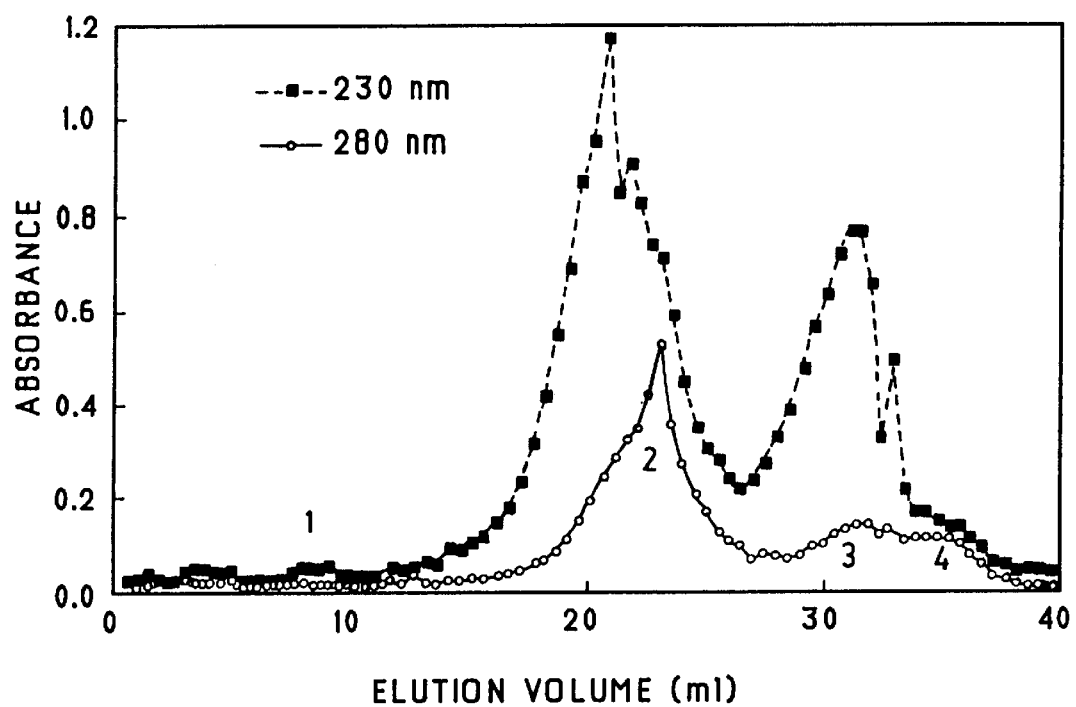
FIG. 7 illustrates fractionation of extracellular extracts from cold acclimated leaves by column chromatography.

Extracellular extracts were concentrated five-fold, exchanged into 50 mM $NH_4HCO_3$ by ultrafiltration (Centriprep-10, Amicon Canada Ltd., Oakville, ON, Canada) and applied to a Sephacryl 200 (Pharmacia LKB Biotechnology, Uppsala, Sweden) column (0.5×32 cm) in 50 mM $NH_4HCO_3$. The eluate was monitored for UV absorbance at 280 nm (○ -- ○) and 230 nm (■ -- ■). Proteins standards were eluted separately to estimate protein size. Ferritin, 440 kD, eluted at 9.5 ml; aldolase, 158 kD, eluted at 11.5 ml: bovine serum albumin, 67 kD, eluted at 13.5 ml: and trypsinogen, 24 kD, eluted at 16.5 ml. As shown in FIG. 7, four peaks were observed with apparent molecular masses of 305 kD (peak 1), 5 kD (peak 2), 2 kD (peak 3) and <1 kD (peak 4). Only fractions associated with peak 2 formed hexagonal and bipyrimidal ice crystals upon testing fraction antifreeze properties.

SDS-PAGE of polypeptides

Figure 9:
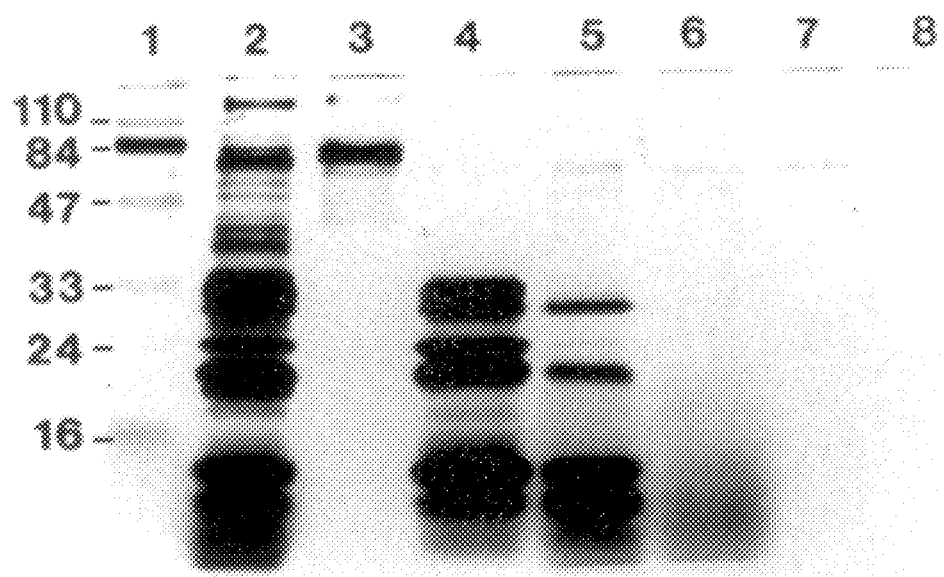
FIG. 9 is an SDS-PAGE of polypeptides associated with column fractions of each 280 nm peak shown in FIG. 8.

The polypeptides associated with column fractions of each of the peaks for 280 nM as shown in FIG. 7 were evaluated. The 13.5% acrylamide gel was silver-stained as shown in FIG. 9. Lane 1 is prestained molecular mass standards; lane 2 is crude intercellular extract; lane 3 is polypeptides eluted at 8 ml (peak 1); lane 4 is polypeptides eluted at 18 ml (shoulder of peak 2); lane 5 is polypeptides eluted at 22 ml (peak 2); lane 6 is polypeptides eluted at 26 ml (shoulder of peak 2); lane 7 is polypeptides eluted at 31 ml (peak 3); and lane 8 is polypeptides eluted at 35 ml (peak 4).

Further characterization of polypeptides

Figure 6A:
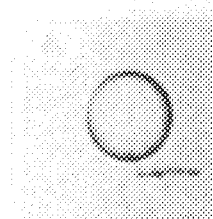
FIG. 6 illustrates the antifreeze activity in extracellular extracts of cold acclimated winter rye leaves. Antifreeze activity was determined by observing ice crystal morphology using a nanoliter osmometer (Clifton Technical Physics, Hartford, N.Y., U.S.A.) (II-5). (A) ice crystal formed in distilled $H_2O$ oriented so that the basal plane is parallel to the plane of the page. (B) ice crystal formed in an apoplastic extract from nonacclimated winter rye leaves. Orientation of the ice crystals in C, D, E, F: the a-axis represents growth in the basal plane and the c-axis represents growth normal to the basal plane. (G) is a hexagonal column of ice as shown in (F), re-oriented so that the c-axis is perpendicular to the plane of the paper.
Figure 8A:
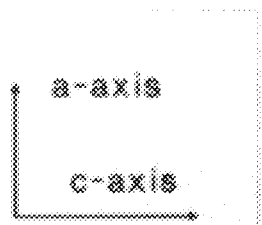
FIG. 8 illustrates the ice crystal morphology of partially purified and concentrated antifreeze protein from cold acclimated winter rye leaves. (A) Orientation of the crystal as described in FIG. 6. (B, C & D) show the growth sequence of an ice crystal as the temperature was lowered: (B) shows an incomplete bipyrimid; (C) shows a bipyrimid; and (D) shows needle-like structures.
Figure 8B:
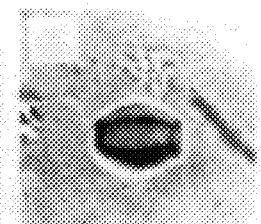
Figure 8C:

Winter rye (Secale cereale cv. Musketeer) is an overwintering, herbaceous monocot that can survive temperatures as low as −35° C. in the field. Rye leaves survive low freezing temperatures by restricting ice to intercellular spaces (II-2). In this experiment, rye seeds were allowed to germinate at 20° C. for one week and the plants then were transferred, either to 20° C. for 3 weeks (nonacclimated) or to 5° C. for 7 weeks, to induce cold acclimation. Under these growth conditions, leaves from nonacclimated plants withstand freezing to −12° C., whereas cold-acclimated leaves can tolerate −22° C. (II-11). Secreted proteins were extracted from the extracellular spaces of winter rye leaves by vacuum infiltration with intercellular washing fluid, followed by centrifugation to recover the infiltrate (II-12). This crude infiltrate was assayed for antifreeze activity by observing the morphology of ice crystals formed in solution using a nanoliter osmometer (II-3,5). In pure water, ice normally grows parallel to the basal plane (a-axes) of the crystal lattice with little growth perpendicular to the basal plane (the c-axis), so that the ice crystals appear flat and round (II-5) (FIG. 6A). In contrast, low (nM) concentrations of antifreeze proteins preferentially inhibit the a-axis growth of ice so that the hexagonal prism faces of the crystal are expressed (II-6) (FIG. 6G). At higher concentrations ($\mu$M) of antifreeze protein, the crystals grow predominantly along the c-axis to form hexagonal bipyramids (II-6) (FIG. 8C).

Figure 6B:
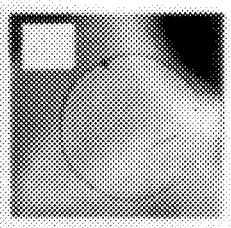
Figure 6C:
Figure 6D:
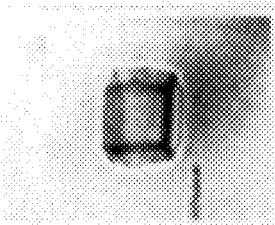
Figure 6E:
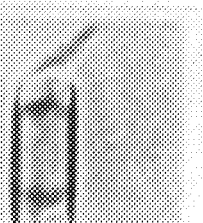
Figure 6F:
Figure 6G:
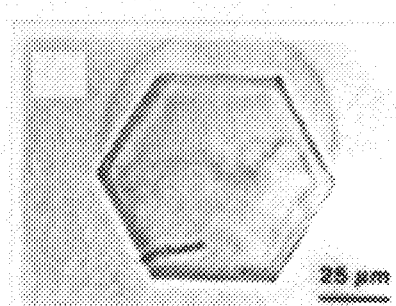

In this experiment, extracellular extracts of nonacclimated rye leaves froze like distilled water; i.e., only thin, round ice crystals were observed (FIG. 6B). In contrast, all crude extracts of the extracellular space of cold-acclimated winter rye leaves formed hexagonal ice crystals upon freezing (FIGS. 6C to 6G). As the temperature was lowered, the crystals expanded first along the c-axis to form incomplete hexagonal bipyramids (FIG. 6C) and then along the a-axis to form both hexagonal columns (FIG. 6D) and larger hexagonal plates of ice (FIGS. 6E to 6G). The formation of hexagonal ice and growth of the ice crystals along the c-axis indicate that antifreeze activity is present in these crude extracts of winter rye (II-3, 5). Furthermore, the fact that these effects on ice crystal morphology were lost when extracellular extracts from cold-acclimated rye leaves were incubated with 5% (w/v) *Streptomyces griseus* protease (Sigma Chemical Co., St. Louis, Mo., U.S.A.) at 22° C. for one hour suggests that the antifreeze activity in winter rye is derived from a protein.

Antifreeze Mechanism

Antifreeze proteins lower the freezing temperature of a solution noncolligatively by binding to ice crystals and inhibiting crystal growth, but the proteins alter the melting temperature of the solution only by colligative effects (II-5). This thermal hysteresis (the difference between freezing and melting temperatures) is determined by observing the effect of temperature on the growth of a single ice crystal. Melting occurs when faces of the ice crystal become round; freezing occurs when the ice crystal elongates along its c-axis (II-5).

Figure 8D:
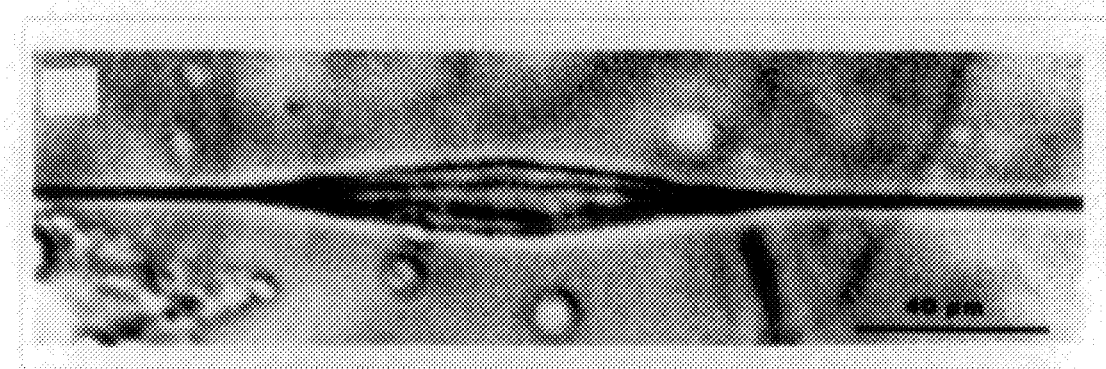

In order to demonstrate thermal hysteresis, we used ultrafiltration, followed by size fractionation on a Sephacryl 200 column, to partially purify proteins contained in the extracellular extracts from cold-acclimated leaves. We obtained four peaks of absorbance at 280 nm with apparent molecular masses of 305, 5, 2 and <1 kD (FIG. 7). These molecular sizes are inaccurate, possibly because the proteins interact with the Sephacryl and so their elution is retarded and they appear smaller in size than they are. Only fractions containing the second (5 kD) peak (FIG. 7) formed bipyrimidal ice crystals in the antifreeze assay. Column fractions exhibiting both absorbance at 280 nm and antifreeze activity (peak 2) were pooled, lyophilized and resolubilized in distilled water for the determination of thermal hysteresis. At this higher protein concentration, ice crystal growth was inhibited along the a-axis (FIGS. 8B to 8D). Furthermore, the ice crystals spiked along the c-axis (FIG. 8D) at an average freezing temperature of $-1.10°$ C. for five ice crystals. The average melting temperature was $-0.78°$ C., and so the thermal hysteresis was calculated to be $0.33±0.06°$ C. (mean±S.D., n=5). Thus, winter rye leaves produce antifreeze protein that has the ability to modify the normal growth pattern of ice and to depress the freezing temperature of a solution noncolligatively.

The thermal hysteresis exhibited by the winter rye antifreeze protein is smaller than that observed for other antifreeze proteins such as found in polar fish (approximately 0.6°) (II-7) or in insects (5° C.) (II-7,II-8). This may be due to the fact that the antifreeze proteins from winter rye are not completely purified or to a difference in structure and function.

SDS-PAGE Analysis of Antifreeze Polypeptides

The results shown in FIG. 9 by SDS-PAGE (13.5% acrylamide), demonstrate that the peak 2 fractions of FIG. 7 with antifreeze activity contain several major polypeptides ranging in size from 5 to 36 kD (FIG. 9, lane 4 and Table I and II). In addition to the polypeptides exhibiting antifreeze activity, the 30 kD polypeptide is also an endoglucanase. The 30 kD band sometimes appears as a 31 to 33 kD band thought to be an endoglucanase precursor. The several major winter rye polypeptides found in column fractions exhibiting antifreeze activity (FIG. 10) are relatively enriched in glycine, asparagine or aspartate, alanine, glutamine or glutamate and serine (see Table III for all of the polypeptides) but do not contain hexosamines (within the limits of detection by amino acid analysis after 4 h hydrolysis of 15 picomoles of each polypeptide). None of the polypeptides exhibits the high alanine content characteristic of antifreeze glycoproteins and type I antifreeze proteins (II-10). Instead, the rye polypeptides exhibit high hydrophilic amino acid contents, as observed in sea raven and ocean pout (II-4), and also contain the high glycine content observed in some insect antifreeze proteins (II-17) (Table III).

When proteins are eluted off the Sephacryl column, low ice nucleation activity is detected in peak 1 and peak 4, of FIG. 7, with higher levels of activity observed in peak 3. SDS-PAGE separated out two polypeptides at molecular weights of about 60 and 68 kD. The ice nucleating protein can be one or a combination of these two polypeptides. These two polypeptides are distinct from the 77 and 73 kD polypeptides shown in FIGS. 2, 3 and 4 because the 60 and 68 kD polypeptides stain blue with Coomassie blue.

Figure 10:
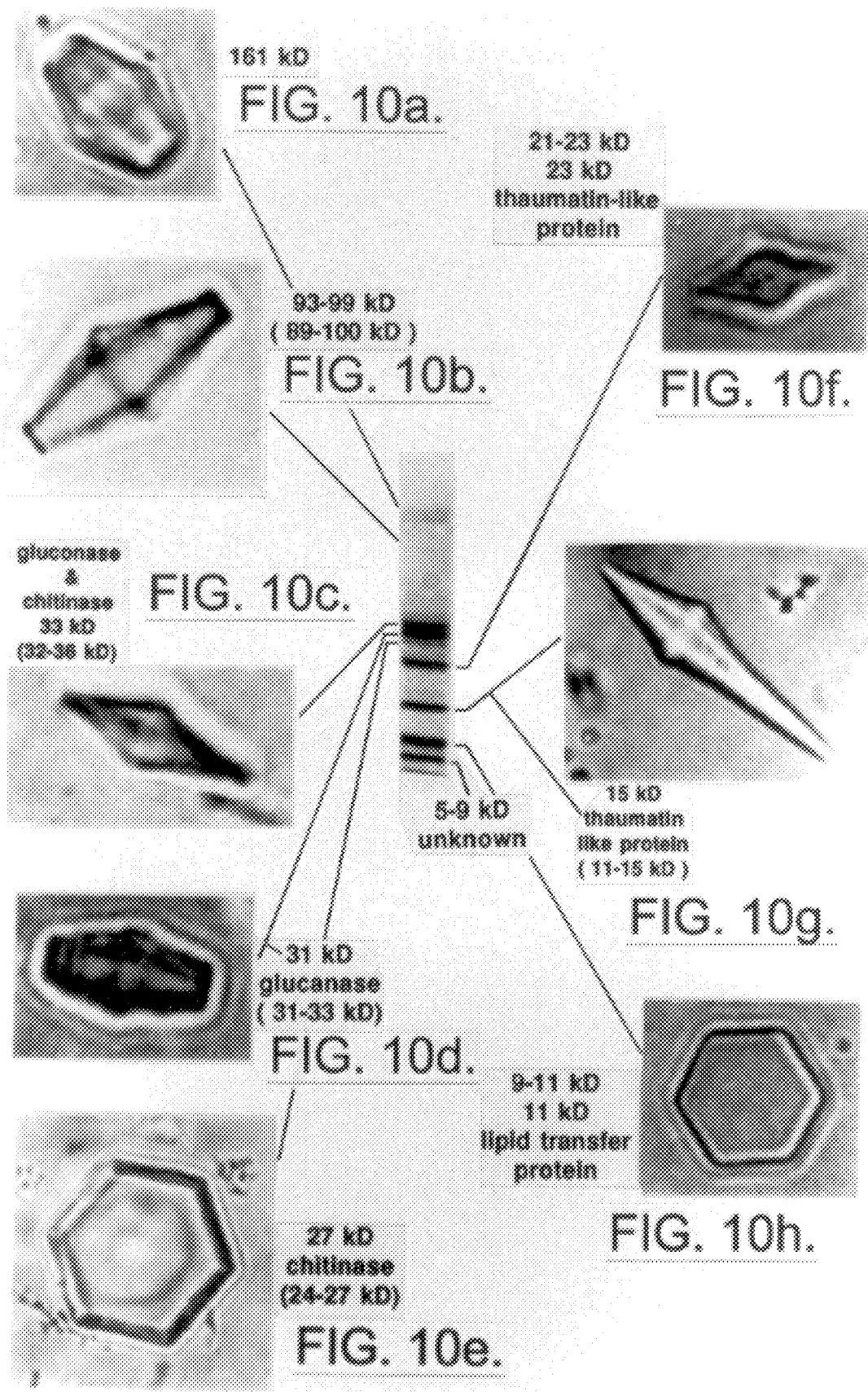
FIG. 10. Apoplastic polypeptides from cold-acclimated winter rye leaves were separated by SDS-PAGE using Tris-tricine buffers. The polypeptides were eluted from the gel and assayed for activity. The (a) 161, (b) 93 to 99, (c) 33, (d) 31, (e) 27, (f) 23, (g) 15 and (h) 11 kD polypeptides all exhibited antifreeze activity.

Antifreeze activity of at least 11 of the polypeptides which accumulate outside the cells at low temperature Extracellular polypeptides were extracted from the apoplast of winter rye leaves using 20 mM $CaCl_2$ and 10 mM ascorbate and were separated by SDS-polyacrylamide gel electrophoresis using a Tris-tricine buffer system with no reducing agent (no dithiothreitol) and large (16×18×0.15 cm) 12% acrylamide gels. The polypeptides were visualized in the gels after a 10 min incubation in ice-cold 0.25M KCl. After washing the gel in distilled $H_2O$, the bands were cut and eluted from the gel in 0.1% SDS and 50 mM Tris-HCl. The polypeptides were precipitated from the elution buffer in 80% acetone at $-20°$ C., pelleted and air-dried. The polypeptides were then redissolved in 0.1M $NH_4HCO_3$ and assayed individually for antifreeze activity by observing changes in ice crystal morphology. As shown in FIG. 10, 8 polypeptides, ranging from 111 to 161 kD in molecular mass, altered the normal pattern of ice crystal growth so that hexagonal ice crystals were formed. The "93 kD" polypeptide actually represents a group of polypeptides that exhibit antifreeze activity and are in the size range of 93 to 99 kD in the Tris-tricine gel system. These polypeptides are distinguished by the fact that they stain a reddish-purple color with Coomassie brilliant blue. In the earlier experiment, polypeptides were separated using a Tris-glycine buffer system and either 12.5% gels or gradient gels, and so the sizes of the polypeptides are somewhat different in this system compared to those of the earlier gels.

Identification of extracellular proteins by Western blot analysis

Apoplastic polypeptides were separated by SDS-PAGE and electroblotted onto nitrocellulose. The blots were probed with primary antibodies to chitinase obtained from Dr. Michel Legrand, Laboratoire de Virologie, Institut de Biologie Moleculaire et Cellulaire de la Recherche Scientifique, 15, rue Descartes, 67000 Strasbourg, France. (I-10.1) The gels and/or blots were probed with a secondary antibody (anti-rabbit IgG conjugated with alkaline phosphatase) for visualization. The results show that there are two extracellular polypeptides, 27 and 32 kD, which have an epitope similar to that of chitinase (FIG. 11). The 27 kD polypeptide is expressed at higher levels in cold-acclimated leaves than in nonacclimated leaves, whereas the 32 kD polypeptide is induced by low temperature. A second Western blot is presented as FIG. 12. The lanes in this blot represent apoplastic polypeptides from winter rye plants grown at 5° C. for 2, 5, 6, 7, 8, and 9 weeks, which were probed with the antibody to chitinase. The 27 kD chitinase is not apparent in leaves of 2-week-old plants, but accumulates during the entire 9 week period. The 32 kD chitinase only becomes apparent after the plants have grown at 5° C. for 7 weeks. At 9 weeks, both chitinase polypeptides appear as doublets (32 and 31 kD, 27 and 26 kD).

Recrystallization inhibition.

Figure 13:
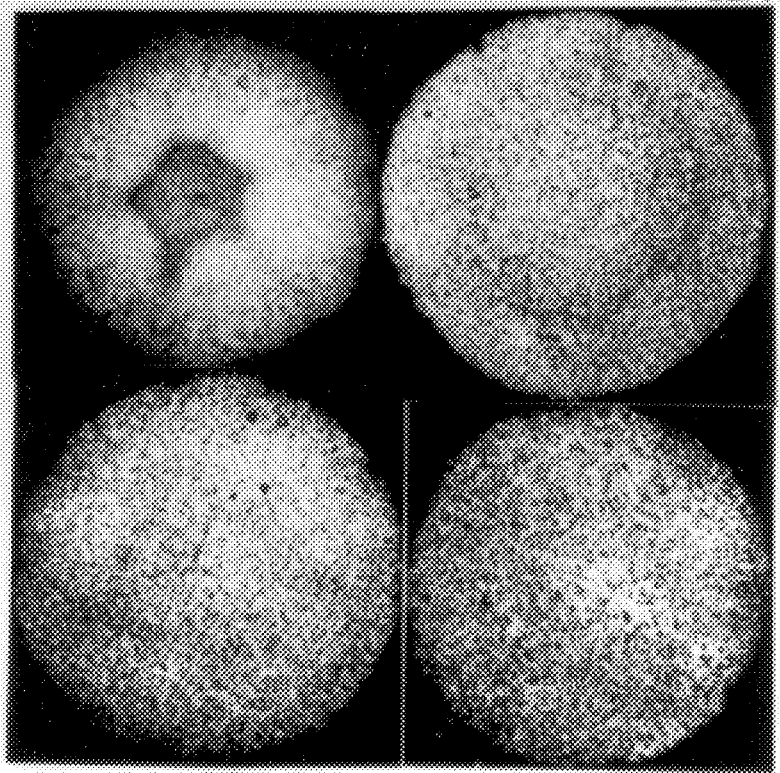
FIG. 13. Recrystallization inhibition of apoplastic extracts obtained from cold-acclimated winter rye plants. At a 1:10,000 dilution, the protein concentration was approximately 28 ug/L. Splats were formed at −20° C. and were annealed at −8° C. for 6 hours.

One role of antifreeze proteins in frost tolerant plants and organisms is to prevent the recrystallization of ice. Although ice may initially form as small crystals, these crystals can amalgamate into larger ice crystals over time and cause mechanical damage to the tissue in the absence of our antifreeze proteins. Recrystallization was assayed by the "splat assay" where a small volume of an apoplastic extract was dropped onto a surface at −20° C. to form a thin layer of small ice crystals. The splat was then annealed at −8° C. for 6 hours. The size of the ice crystals in apoplastic extracts of this invention and in distilled water were compared after annealing to determine whether the extracts 1 were able to inhibit the recrystallization observed in water (FIG. 13). The crystals present in all dilutions of the apoplastic extracts were still significantly smaller than the crystals observed in water after annealing. Thus the apoplastic extracts exhibited significant recrystallization inhibition at a dilution of 1:10,000, which represents a concentration of approximately 28 ug of protein per liter.

Role of apoplastic polypeptides in frost tolerance in rye.

Figure 14:
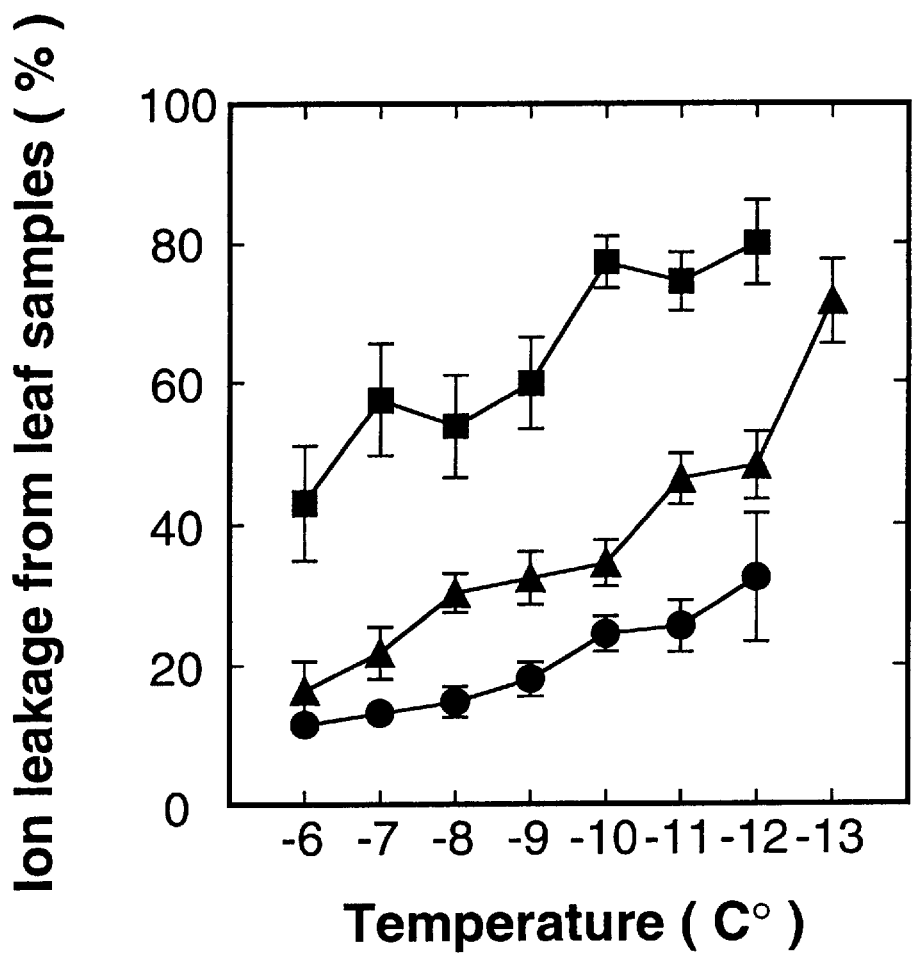
FIG. 14. Ion leakage of nonacclimated leaves (■), cold-acclimated-SD leaves (●) and cold-acclimated-SD leaves which were extracted to decrease the levels of apoplastic proteins (▲). The leaves were placed in water, cooled to the temperature (°C.) at which ice formation occurred and then held at that temperature for 22 min. Leaves were removed from the freezing bath and allowed to thaw slowly on ice. Ion leakage was calculated as the conductivity of the solution after the leaves were frozen divided by the total conductivity of the solution after boiling. The data were corrected for ion leakage of unfrozen samples and are presented as means±SE, n=3.

Winter rye leaves that had been cold-acclimated at 5° C. with an 8 hour daylength were extracted with 20 mM $CaCl_2$ and 10 mM ascorbic acid to reduce the protein concentration present in the apoplast. Nonacclimated rye leaves (grown at 20° C.), cold-acclimated leaves and cold-acclimated leaves that had been extracted were cut into 2.5 cm lengths and rinsed well with distilled water. For each of the three treatments, leaf pieces were placed in each of 50 tubes containing 4 mLs HPLC-grade water. The tubes were positioned in a freezing bath, and the temperature was lowered at 1° C. intervals every 22 min. At each temperature, the number of samples which had frozen were removed and placed on ice to thaw slowly. The samples were then brought to room temperature and the conductivity of the samples was measured. The samples were boiled to release all internal ions, cooled to room temperature, and the conductivity of the solution was measured again. The results are shown in FIG. 14. Extraction of the apoplastic proteins caused lethal freezing injury to occur at −11° C. in cold acclimated leaves. Unextracted cold-acclimated leaves normally survive temperatures as low as −30° C. when ice formation occurs at −1° C. When the unextracted cold-acclimated leaves are allowed to freeze spontaneously, they are not killed at temperatures above −13° C. Thus the presence of proteins in the apoplast does decrease the level of injury caused by freezing.

N-Terminal Amino Acid Sequence Analysis

Partial amino acid sequences for 3 of the seven major polypeptides shown in lane 4 of FIG. 9 were determined.

The 9 kD polypeptide that exhibits antifreeze activity has been partially sequenced. The sequence representing the first twenty amino acids of the N-terminus of the polypeptide:

$NH_2$-ALA-ILE-PHE-CYS-GLY-GLN-VAL-ASN-PRO-ALA-LEU-GLY-PRO-PRO-ILE-TYR-PRO-ALA-PHE-GLY-(SEQ ID NO:1).

The first 16 amino acids of the 11 kD polypeptide are:

$NH_2$-ARG-SER-PHE-SER-ILE-THR-ASN-ARG-CYS-TRP-SER-PHE-THR-VAL-PRO-GLY-(SEQ ID NO:3)

The first 11 amino acids exhibit 55% homology with a kinase-related transforming protein (listed under the file names MUSHCK and TVMSHC).

The first 30 residues of the N-terminal sequence for the 31 kD protein are as follows:

wherein X indicates an unknown amino acid residue.

This sequence was checked for homology with protein sequences listed in the National Cancer Institute's Supercomputer databanks. This sequence has 63% homology with the glucan endo-1,3-beta-glucosidase (EC 3.2.1.39) previously purified from barley. These results suggest that one of the mechanisms involved in the development of frost tolerance is a modification of the cell wall to increase its flexibility. The cell wall must conform to the protoplast as it shrinks during extracellular ice formation.

Additional amino acid sequences were obtained for six extracellular polypeptides which exhibit antifreeze activity. The polypeptides were separated by SDS-PAGE using Tritricine buffers, eluted from the gels, assayed for antifreeze activity, as shown in FIG. 10, and then used for sequence analysis. The N-terminal sequences are as follows:

11 kD polypeptide:
$NH_2$−ALA−ILE−SER−X−GLY−GLU−GLN−VAL−ASN−SER−ALA−LEU−[GLY]−PRO−X−ILE−[SER]−TYR−ALA−[ARG]−[GLY] (SEQ ID NO.2).

A fasta search of the Protein Information Resource revealed that this sequence has 80% identity in the 20 amino acid overlap area with a lipid transfer protein from barley with a molecular mass of 9 kD (II-14.2). This 11 kD polypeptide from FIG. 10 corresponds to the 9 kD polypeptide in FIG. 9 that was sequenced above. As noted above, this divergence in molecular weight is due to the variability in the gel analysis.

15 kD polypeptide:
$NH_2$−ARG−SER−PHE−SER−ILE−THR−ASN−ARG−X−ALA−PHE−THR−VAL−X−PRO−ALA−ALA−THR−PRO−VAL−GLY−GLY−GLY−GLY−GLN (SEQ ID NO.4)

A fasta search of the Protein Information Resource of the National Biomedical Research Foundation revealed that this sequence has 75% identity in a 24 amino acid overlap with the reported sequence for a thaumatin-like protein from oryza sativa. This 15 kD polypeptide from FIG. 10 may correspond to the 11 kD polypeptide from FIG. 9 sequenced above.

23 kD polypeptde:
$NH_2$−ALA−THR−ILE−THR−VAL−VAL−ASN−[LYS]−PHE−SER−TYR−THR−VAL−X−PRO−GLY−ALA−LEU−PRO−PHE−GLY−GLY−VAL−GLY−LEU−GLY−PRO−GLY−GLN−(SEQ ID NO.5)

A fasta search revealed that this sequence has 79% identity in a 29 amino acid overlap with thaumatin homolog protein 1 from barley. It also has 77% homology in a 22 amino acid overlap with avematin isolated from oat and 82% identity in a 22 amino acid overlap with trimatin isolated from wheat. Thaumatin-like proteins have been shown to exhibit a number of activities, including alpha-amylase, protease and membrane permeabilizing activities (II-8.2).

32 kD polypeptide in FIG. 10 which corresponds to the 30 kD polypeptide in FIG. 9 for which a longer amino acid sequence is described above:

$NH_2$−ILE−GLY−VAL−CYS−TYR−GLY−VAL−ILE−GLY−ASN−ASN−LEU−PRO−SER−ARG−SER−ASP−VAL−VAL−GLN−LEU−TYR−ARG−SER−GLY−X−ILE−ASN−X−MET−(SEQ ID NO: 6)

NH$_2$—ILE—GLY—VAL—X—TYR—GLY—VAL—ILE—GLY—ASN—ASN—LEU—PRO—[SER]—ARG—[SER]—ASP—VAL—VAL—GLU (SEQ ID NO.8)

33 kD polypeptide:
NH$_2$—GLU—GLN—X—GLY—SER—GLN—ALA—GLY—GLY—ALA—THR—X—PRO—ASN—ASN—LEU—LEU— (SEQ ID NO.7)

A fasta search revealed that this sequence has 81% identity in a 16 amino acid overlap with hevein from the para rubber tree. The sequence also has 88% identity in a 16 amino acid overlap with endochitinase (EC 3.2.1.14) isolated from rice and tobacco, as well as 92% identity in a 14 amino acid overlap with agglutinin from wheat also known as isolectin 11.

Antifreeze Activity in Different Parts of Plants

Winter rye plants grown at 5° C. were separated into leaves, crowns and roots. These parts of the plants were placed in plastic bags, frozen in liquid nitrogen and allowed to thaw at room temperature. The plant tissues were then treated to obtain soluble fractions. These fractions were then assayed for their ability to modify ice crystal growth. The soluble fractions of leaves, crowns and roots all exhibited the formation of hexagonal bipyrimids in the assay for antifreeze activity. These results demonstrate that antifreeze activity is present in all parts of the vegetative plant.

Different Species and Cultivars Having Antifreeze Activity

Sixteen different species or cultivars including both monocots and dicots (see Table IV) were grown at 5°/2° C. (day/night temperature) with a 16 hour daylength. Leaves from all sixteen plants were extracted by vacuum infiltration followed by centrifugation using a solution of 20 mM $MgCl_2$ and 10 mM ascorbic acid, pH 3.5. All sixteen intercellular extracts exhibited the ability to modify the normal pattern of ice crystal growth, although this ability varied between cultivars and species. Of the plants tested, winter rye (*Secale cereale* cv. Musketeer), periwinkle (*Vinca minor*), winter wheat (*Triticum aestivum* cv. Karat and Ruby) and winter barley (*Hordeum vulgare* cv. Acton) extracts exhibited the greatest effect on ice crystal growth with the formation of hexagonal bipyrimids, whereas winter canola (*Brassica napus* cv. Ceres) extract exhibited the least effect with only the formation of hexagonal discs.

Polypeptides Having Glucanase Activity

Extracellular extracts of winter rye leaves were obtained using an extraction solution of 20 mM calcium chloride and 10 mM ascorbic acid, pH 3.5. Beta-1,3-glucanase activity was measured in extracellular extracts using the dinitrosalicylic reagent to assay the release of glucose equivalents from laminarin (II-1.0). In our experiments, the glucanase assay was optimal under the following conditions: pH 3.5, 1% laminarin, presence of $CaCl_2$ (as opposed to $MgCl_2$ or $MnCl_2$), 5° C., and measuring absorbance of 470 nm. In crude extracellular extracts, the beta-1,3-glucanase activity was approximately 312 mg glucose equivalents per mg total protein per hour. The extract did not exhibit beta-1,4-glucanase activity when carboxymethylcellulose was used as a substrate.

In crude extracellular extracts, the endochitinase activity (I-10.1) was 115 nmol glucosamine released per gram fresh weight per hour, and the exochitinase activity was 9 nmol glucosamine released per gram fresh weight per hour in winter rye plants grown at 5° C. with a short day. Rye plants grown at 20° C. exhibited an endochitinase activity of 34 nmol glucosamine released per gram fresh weight per hour and an exochitinase activity of less than 3 nmol glucosamine released per gram fresh weight per hour.

Ice Nucleation Activity

Suspensions of single mesophyll cells were obtained from 20° C. and 5° C. winter rye leaves by pectolytic degradation of the leaf tissue and purification using density gradients as described in detail by Line Lapointe (1991. Photoinhibition of hardened and nonhardened rye (*Secale cereale* cv. Musketeer) studied with isolated thylakoids, isolated mesophyll cells, and intact leaves. In order to quantify the number of ice nucleators present in winter rye, dilution series of the single cell suspensions were assayed for ice nucleation activity using the droplet technique. The mean threshold ice nucleation temperature for mesophyll cells isolated from 20° C. and from 5° C. leaves was not significantly different and averaged −7.3° C. The mean number of mesophyll cells required to obtain an ice nucleator active at −7° C. was 35,000 for 20° C. leaves which can tolerate −7° C., 29,000 for 5° C./16 hour daylength leaves which can tolerate −19° C., and 11,000 for 5° C./8 hour daylength leaves which can tolerate −30° C. The results are set out in Table V.

The composition of the ice nucleators from leaves of frost tolerant plants grown under different conditions was determined by incubating single cells in the presence of compounds and enzymes known to affect proteins, sulfhyryl groups and disulfide bonds associated with proteins, carbohydrates and phospholipids. The results are set out in Table VI. The effect of the compound or enzyme on the ice nucleator was determined by assaying ice nucleation activity. Treating cells with 3M urea and heating to 90° C. denatures proteins and dramatically decreases ice nucleation activity. Nonspecific proteases (Pronase E and Proteinase K) also decreased ice nucleation activity. Thus the ice nucleators associated with winter rye mesophyll cells have a proteinaceous component. Reduction of disulfide bonds with dithiothreitol and reaction of free sulfhydryl groups with N-ethylmaleimide also decreased ice nucleation activity, which shows that the structure of the protein is important in producing ice nucleation activity. Boric acid and periodic acid both react with carbohydrates and both compounds reduce ice nucleation activity, thus demonstrating that the ice nucleators also contain a carbohydrate component. Finally, treatment with phospholipase C, which releases the phosphate and head group of phospholipids, also decreased ice nucleation activity. Taken, together, these results suggest that ice nucleators associated with winter rye mesophyll cells have protein, carbohydrate and phospholipid components.

Antibodies to the Polypeptides

Polyclonal and monoclonal antibodies can be prepared for polypeptides present in extracellular extracts from cold-hardened winter rye leaves, such as the aforementioned antibodies to the chitinase polypeptides. Individual polypeptides separated by SDS-PAGE and electroeluted from gel slices are used as antigens. The antibodies are purified and used for immunopurification of the polypeptides in order to determine the ice nucleation, antifreeze and glucanase activity of each. Furthermore, the antibodies can be used for immunoassays of the polypeptides. The procedures for antibody production and purification, immunopurification of antigens and immunoassays are described in detail by Harlow and Lane (II-8.1). The detection and quantification of these polypeptides can be used in selection programs designed to decrease plant injury and yield losses caused by freezing temperatures. Previous selection programs have relied on winter survival to increase frost tolerance in overwintering crops and have been unsuccessful. Because of their sensitivity, the immunoassays provide a nondestructive means for selecting plants that have high concentrations of polypeptides associated with either freezing avoidance (presence of antifreeze and glucanase protein and absence of ice nucleators) or frost tolerance (presence of ice nucleation, antifreeze and glucanase protein). Furthermore, these antibodies may be bound to the polypeptide to enhance the antifreeze activity of the subject polypeptides.

Discussion of Experimental Findings

The ice nucleation activity of the isolated polypeptides occurs in the intercellular spaces of the plant tissue. It appears that the ice nucleation proteins are bound to the cell wall and were released only by reagents that reduce disulfide bonds. This treatment also reduced ice nucleation activity.

As demonstrated by the further characterization of the polypeptides at least 11 polypeptides are synthesized at low non-freezing temperatures, namely those of lane 4 of FIG. 9 and FIG. 10 ranging in molecular weight from 5 kD to 36 kD and the additional polypeptides of 60, 68 kD, 93 to 99 kD and 161 kD. We have determined that three of the polypeptides, the enzymes glucanase and the two chitinases and the thaumatin-like proteins have an unexpected antifreeze property. Also these polypeptides along with the other polypeptides of this invention exhibit recrystallization inhibition activity at very low concentrations.

It is important to note the results of FIG. 3 where a time course examines changes in intercellular proteins of rye leaves during cold acclimation. A co-relation exists between the degree of cold hardiness and the increased appearance of the extracellular polypeptides. The intensity of the extracellular polypeptides reaches a maximum at 78 days which corresponds to the hardiest stage of rye plants cold acclimated with a day length of 8 hours. Most of the extracellular polypeptides decrease in intensity while others were no longer detected at 102 days after germination. This result indicates the loss of freezing tolerance when plants are exposed to extended spring-like conditions. Ice nucleation activity is also indicated in Table V at levels as high as −7° C. This is believed to be the first report of ice nuclei of proteinaceous nature in higher plants. It is also likely that several ice nucleating molecules are required in the assembly of a template upon which an ice crystal can grow. It is understood that the ice nucleating proteins are important in the extracellular spaces for the development of freezing tolerance in cold acclimated leaves.

The polypeptides as isolated and characterized in accordance with this invention establish that plants withstand frost by the combined efforts of ice nucleation, ice crystal modification by virtue of antifreeze mechanism and enzymatic alteration of the cell walls to allow the cell walls to increase flexibility during development of ice crystals in the intercellular spaces. It has been demonstrated that cold acclimated winter rye leaves are not injured by ice formation even when the leaves are first undercooled to temperatures as low as −12° C. Non-acclimated winter rye leaves exhibit injury whenever ice forms. Hence, in the development of frost tolerance a gradual acclimation is required. In accordance with this invention, ice formation in the extracellular spaces indicates that it is not the presence of antifreeze proteins which determines the lowest limit of cell survival at freezing temperatures. As temperatures decrease intracellular water is lost to the growing extracellular ice masses and the cells themselves become dehydrated. The lowest temperature which frost tolerant plants survive is therefore correlated with desiccation tolerance of the cells (II-16, 18).

Conventional breeding programs have failed to improve frost resistance in crop plants because physiological markers specific for frost tolerance are not yet available (II-2). The discovery of ice nucleation and antifreeze proteins intrinsically produced by a frost tolerant plant as demonstrated by this invention represents an important breakthrough in agriculture for two reasons. First of all, the ice nucleation and antifreeze polypeptides are the first polypeptides demonstrated to be directly involved in the process of freezing tolerance in plants. Antifreeze and ice nucleation polypeptides may prove useful as selection markers for increasing frost tolerance in overwintering crops. Secondly, further isolation and characterization of the ice nucleation and antifreeze protein will be useful for increasing survival and productivity. In the future, it may be possible to raise crops successfully in regions or in seasons where crop production is now limited by freezing temperatures.

As already indicated the polypeptides are useful in production of frozen foods and cryogenic storage of biological tissues. Treatment of frozen foods with the polypeptides can ensure superior food quality upon thawing of the product. Also, with the manufacture of products such as ice cream as well as in the cryopreservation of biological tissues it is desirable to have a minute crystalline structure. The use of the antifreeze proteins in limiting crystalline size and in preventing recrystallization would be very useful in providing a superior product. The amount of polypeptides used in these biological matter and food compositions is minimal, as demonstrated in the examples. For example, an effective amount of the polypeptide may be as little as 25 μg of the polypeptide per liter of contained water in the biological matter or food product.

Although preferred embodiments of the invention are described herein in detail, it will be understood by those skilled in the art that variations may be made thereto without departing from the spirit of the invention or the scope of the appended claims.

TABLE I

Comparison of Extracellular Polypeptides from Winter Rye

POLYPEPTIDES (Molecular Mass in kD)

| Extract # | Bands Stain Blue with Coomassie Brilliant Blue Stain | | | | | | | | | Bands Stain Red-Purple | | | Blue |
|---|---|---|---|---|---|---|---|---|---|---|---|---|---|
| 1 | | 9 | | 18 | 24 | 29 | 31 | | | | 73 | 77 | | 109 |
| 2 | | 10 | 13 | 17 | 23 | 31 | 32 | | | | 71 | 75 | 100 | |
| 3 | 5 | 9 | 11 | 22 | 24 | 30 | | 36 | 60 | 68 | | | | |
| 4 | | 9 | 11 | 22 | 24 | 30 | | 36 | | | | | | |

TABLE I-continued

Comparison of Extracellular Polypeptides from Winter Rye

POLYPEPTIDES (Molecular Mass in kD)

| Extract # | Bands Stain Blue with Coomassie Brilliant Blue Stain | | | | | | | | | | Bands Stain Red-Purple | | Blue |
|---|---|---|---|---|---|---|---|---|---|---|---|---|---|
| 5 | 12 | 14 | 15 | 21 | 25 | 30 | 33 | 36 | | | 72 | 89 | |
| 6 | | 9 | 11 | 22 | 24 | 30 | | 36 | | | | | |
| 7 | | | | | 27 | | | 32 | | | | | |
| 8 | 5 | 11 | 15 | 23 | 27 | 31 | 32 | 33 | | | | 93  99 | 161 |
| Polypeptide | A | B | C | D | E | F | G | H | I | J | K  L | M | N |
| SUMMARY | 5 to 9 | 9 to 11 | 11 to 15 | 21 to 22 | 24 to 27 | 30 to 31 | 31 to 33 | 32 to 36 | 60 | 68 | 71 to 73  75 to 77 | 89 to 100 | 161 |

NOTE: Sources of variability in estimating molecular masses (kD) of the individual polypeptides include:
1. Use of different extraction buffers
2. Use of crude extracts versus fractions obtained from column chromatography
3. Differences in acrylamide concentrations of the gels
4. Use of prestained versus unstained markers
5. Difficulty in extrapolating the data to estimate molecular masses (kd) for polypeptides bigger than or smaller than the standard proteins used
6. Differences in protein loading of the gels (some are obviously overloaded)
7. Molecular mass determinations made by different people
8. Presence or absence of reducing agent in the solutons for SDS-PAGE
9 Different running buffers for SDS-PAGE: Tris-glycine versus Tris-tricine

TABLE II

Summary of Information about the Extracellular Polypeptides Induced by Low Temperature in Winter Rye

| POLY-PEPTIDE OF TABLE I | (kD) | ICE-BINDING ACTIVITY | IDENTITY | SOURCE OF DATA |
|---|---|---|---|---|
| A | 5–9 | unknown | unknown | SDS-PAGE |
| B | 9–11 | antifreeze | lipid transfer protein | SDS-PAGE, N-terminal sequence |
| C | 11–15 | antifteeze | thaumatin-like | SDS-PAGE, N-termmal sequence |
| D | 21–23 | antifreeze | thaumatin-like | SDS-PAGE, N-terminal sequence |
| E | 24–27 | antifreeze | chitinase | SDS-PAGE, N-terminally blocked, Western Blot |
| F | 30–31 | antifreeze | glucanase | SDS-PAGE, N-terminal sequence |
| G | 31–33 | antifreeze | glucanase | SDS-PAGE, N-terminal sequence |
| H | 32–36 | antifreeze | glucanase and chitinase | SDS-PAGE, N-terminal sequence Western Blot |
| I | 60 | ice nucleator | unknown | SDS-PAGE, column chromatography |
| J | 68 | ice nucleator | unknown | SDS-PAGE, column chromatography |
| K | 71–73 | unknown | thought to be oligomers of glucanase (data not presented) | SDS-PAGE |
| L | 75–77 | unknown | | SDS-PAGE |
| M | 89–100 | antifreeze | | SDS-PAGE |
| N | 161 | antifreeze | | SDS-PAGE |

TABLE III

Amino Acid Compositions (mol %) of 8 Extracellular Polypeptide Extracts of Table I, 7 of which Have Been Identified by N-Terminal Sequencing of the Amino Acids

| | ABBREVIATED NAME OF POLYEPEPTIDES | | | | | | | |
|---|---|---|---|---|---|---|---|---|
| | B | C | D | E | F | G | H | M |
| | MOLECULAR MASS OF POLYPEPTIDES | | | | | | | |
| | 11 kD | 15 kD | 23 kD | 27 kD | 31 kD | 32 kD | 33 kD | 93–99 kD |
| | IDENTITY OF POLYPEPTIDES | | | | | | | |
| Amino Acid | Lipid Transfer Protein | Thaumatin-like | Thaumatin-like | Chitinase | Glucanase | Glucanase | Glucanase and Chitinase | Un-known |
| ASX | 8.4 | 15.8 | 11.7 | 11.6 | 11.8 | 14.6 | 12.3 | 5.6 |
| GLX | 8.3 | 6.5 | 8.6 | 6.9 | 8.8 | 7.3 | 8.3 | 12.5 |
| SER | 9.1 | 10.0 | 7.8 | 6.9 | 9.2 | 8.8 | 9.6 | 8.4 |
| GLY | 11.8 | 13.6 | 14.9 | 13.4 | 12.0 | 11.0 | 12.6 | 10.9 |
| HIS | 0.0 | 0.0 | 0.0 | 0.6 | 0.0 | 0.0 | 0.0 | 0.0 |
| ARG | 7.9 | 8.1 | 6.1 | 6.2 | 5.1 | 4.9 | 5.3 | 3.2 |
| THR | 8.8 | 9.3 | 11.8 | 9.5 | 6.0 | 6.2 | 7.2 | 5.4 |
| ALA | 14.2 | 8.2 | 8.8 | 11.5 | 12.5 | 11.7 | 10.1 | 9.0 |
| PRO | 9.3 | 6.4 | 9.3 | 5.4 | 6.7 | 7.6 | 7.1 | 16.7 |
| TYR | 2.7 | 2.5 | 2.6 | 5.2 | 3.8 | 4.9 | 4.8 | 2.7 |
| VAL | 4.8 | 3.9 | 4.4 | 4.9 | 5.3 | 5.3 | 5.3 | 3.9 |
| MET | 0.0 | 0.0 | 1.3 | 1.9 | 2.2 | 1.4 | 0.8 | 5.3 |
| CYS | 3.5 | 4.5 | 4.0 | 1.6 | 2.4 | 0.0 | 2.1 | 3.7 |
| ILE | 3.8 | 3.0 | 2.3 | 3.3 | 3.6 | 4.1 | 3.1 | 2.8 |
| LEU | 4.2 | 3.1 | 3.0 | 4.4 | 5.7 | 6.1 | 5.1 | 4.4 |
| PHE | 0.0 | 3.5 | 4.0 | 4.8 | 3.8 | 3.8 | 3.8 | 2.5 |
| LYS | 3.1 | 1.7 | 2.1 | 1.7 | 2.1 | 2.6 | 2.6 | 4.1 |

TABLE IV

Antifreeze of Four Species of Monocotyledonous Plants and Two Species of Dicotylodonous Plants. Protein Concentration and Relative Antifreeze Activity of Extracellular Extracts of Leaves from Plants Grown at 5° C. with a 16 Hour Day

| Species | Cultivar | Protein concentration (mg/g fresh Weight) | Rank of Antifreeze Activity[1] |
|---|---|---|---|
| Monocots Secale Cereale (winter rye) | Muskeeter | 0.15 | 5 |
| Tricium aestivum (wheat) | | | |
| Soft-white Winter | Annette | 0.30 | 3 |
| | Augusta | 0.22 | 2 |
| | Frankenmuth | 0.09 | 2 |
| | Frederick | 0.16 | 4 |
| | Rebecca | 0.04 | 2 |
| Hard-red winter | Absolvent | 0.15 | 4 |
| | Karat | 0.23 | 5 |
| | Ruby | 0.24 | 5 |
| Spring | Katepwa | 0.12 | 4 |
| Hordeum vulgare (winter barley) | Actorn | 0.05 | 5 |
| | Elmira | 0.25 | 3 |
| | Halton | 0.25 | 3 |
| | Huron | 0.11 | 1 |
| Avena sativa (winter oats) | Ogle | 0.04 | 4 |
| Dicots: Brassica napus (winter canola) | Ceres | 0.04 | 1 |
| Vinca minor (periwinkle | | 0.04 | 5 |

[1]Ranks represent increasing antifreeze activity based on ice crystal morphology as follows (1) hexagonal disc, (2) short hexagonal column, (3) long hexagonal column, (4), partial hexagonal bipyramid and (5) complete hexagonal bipyramid.

TABLE V

Comparison Between Hardened and Nonhardened Rye Leaves in the Number of Mesophyll Cells Required to Obtain an Active Ice Nucleator

| Growth Conditions | Number of Replicates | Mean Threshold Nucleation Temperature (Mean ± S.D.) | Mean Number of Cells Per Nucleator (Mean ± S.D.) |
|---|---|---|---|
| Nonhardened Rye (20° C./16 h day) | 12 | −7.2 ± 0.6 | 35,266 ± 25,977 |
| Hardened Rye (5° C./16 h day) | 14 | −7.1 ± 0.8 | 28,511 ± 39,563 |
| Hardened Rye (5° C./8 h day) | 16 | −7.6 ± 0.6 | 10,847 ± 11,211 |

TABLE VI

Characterization of Ice Nucleators Associated with Winter Rye Mesophyll Cells

| Treatment | Indication | GROWTH CONDITIONS | | |
|---|---|---|---|---|
| | | 20° C., 16 hr | 5° C., 16 h | 5° C., 8 hr |
| | | mean threshold ice nucleation temperature = S.D. (n) | | |
| Crude | | −7.2 ± 0.5(15) | −7.2 ± 0.7(17) | −7.4 ± 0.7(19) |
| Boric acid (4 mM) | Carbohydrates | −12.1 ± 0.6(3)[a] | −11.0 ± 0.5(3)[a] | −10.6 ± 1.1(3)[a] |
| Periodic acid (2 mM) | Carbohydrates | −11.4 ± 1.0(3)[a] | −10.7 ± 1.5(3)[a] | −9.4 ± 1.8(5)[a] |
| Phospholipase C (3 mg/ml) | Lipids | −10.8 ± 1.5(3)[a] | −8.7 ± 1.1(3)[b] | −9.5 ± 0.4(7)[a] |
| Heat (90° C. 10 minutes) | Proteins | −10.7 ± 1.6(5)[a] | −12.0 ± 0.5(3)[a] | −11.5 ± 1.8(5)[a] |
| Urea (3M) | Proteins | −11.2 ± 1.5(4)[a] | −11.4 ± 1.2(5)[a] | −13.4 ± 0.1(3)[a] |
| Pronase E (3 mg/mL) | Proteins | −11.1 ± 2.6(3)[a] | −9.3 ± 0.8(3)[a] | −9.1 ± 0.5(7)[a] |
| Proteinase K (3 mg/mL) | Proteins | −7.5 ± 0.4(3)[c] | −10.2 ± 0.1(3)[a] | −10.9 ± 0.7(3)[a] |
| N-ethylmaeimide (1 mM) | —SH groups | −12.2 ± 1.9(5)[a] | −11.1 ± 0.6(3)[a] | −12.1 ± 3.3(3)[a] |
| Dithiothreitol (50 mM) | Disulphides | −9.2 ± 0.7(40[a] | −10.1 ± 1.0(5)[a] | −10.4 ± 1.3(5)[a] |

[a]test of significance at 99.9%
[b]test of significance at 95%
[c]not significantly different from crude

---

I claim:

1. Purified antifreeze polypeptides isolated from the extracellular spaces between the cells of winter rye where said polypeptides control ice crystal growth in the intercellular plant spaces, such control of ice crystal growth providing a degree of plant frost tolerance, said purified polypeptides having the following properties of:
i) being developed in extracellular spaces between plant cells of frost tolerant winter rye plant leaves by low temperature induction of frost tolerant winter rye plant to produce said polypeptides;
ii) being isolated from said extracellular spaces and purified; and
iii) being selected from a group of purified antifreeze polypeptides consisting of polypeptides having respectively apparent molecular weights as determined by SDS-PAGE Gel separation under non-reducing conditions, of about 11 kD, about 15 kD, about 23 kD, about 27 kD, about 31 kD, about 32 kD, about 33 kD, about 93 to 99 kD and about 161 kD.

2. A polypeptide of claim 1 wherein said selected polypeptide is further characterized by an amino acid residue content of the following respective listing:

| Amino Acid | 11 kD | 15 kD | 23 kD | 27 kD | 31 kD | 32 kD | 33 kD | 93–99 kD |
|---|---|---|---|---|---|---|---|---|
| ASX | 8.4 | 15.8 | 11.7 | 11.6 | 11.6 | 14.6 | 12.3 | 5.6 |
| GLX | 5.3 | 6.5 | 8.6 | 6.9 | 5.8 | 7.3 | 8.3 | 12.5 |
| SER | 9.1 | 10.0 | 7.8 | 6.9 | 9.2 | 8.8 | 9.6 | 8.4 |
| GLY | 11.8 | 13.6 | 14.9 | 13.4 | 12.0 | 11.0 | 12.6 | 10.9 |
| HIS | 0.0 | 0.0 | 0.0 | 0.6 | 0.0 | 0.0 | 0.0 | 0.0 |
| ARG | 7.9 | 8.1 | 6.1 | 6.2 | 5.1 | 4.9 | 5.3 | 3.2 |
| THR | 8.8 | 9.3 | 11.8 | 9.5 | 6.0 | 6.2 | 7.2 | 5.4 |
| ALA | 14.2 | 8.2 | 8.8 | 11.5 | 12.5 | 11.7 | 10.1 | 9.0 |
| PRO | 9.3 | 6.4 | 9.3 | 5.4 | 6.7 | 7.6 | 7.1 | 16.7 |
| TYR | 2.7 | 2.5 | 2.6 | 5.2 | 3.8 | 4.9 | 4.8 | 2.7 |
| VAL | 4.8 | 3.9 | 4.4 | 4.9 | 5.3 | 5.3 | 5.3 | 3.9 |
| MET | 0.0 | 0.0 | 1.3 | 1.9 | 2.2 | 1.4 | 0.8 | 5.3 |
| CYS | 3.5 | 4.5 | 4.0 | 1.6 | 2.4 | 0.0 | 2.1 | 3.7 |
| ILE | 3.8 | 3.0 | 2.3 | 3.3 | 3.6 | 4.1 | 3.1 | 2.8 |
| LEU | 4.2 | 3.1 | 3.0 | 4.4 | 5.7 | 6.1 | 5.1 | 4.4 |
| PHE | 0.0 | 3.5 | 4.0 | 4.8 | 3.8 | 3.8 | 3.8 | 2.5 |
| LYS | 3.1 | 1.7 | 2.1 | 1.7 | 2.1 | 2.6 | 2.6 | 4.1 |

3. A polypeptide of claim 2 wherein said selected 15 kD polypeptide has an N-terminal amino acid sequence of:

NH$_2$—Arg—Ser—Phe—Ser—Ile—Thr—Asn—Arg—Xaa—Ala—Phe—Thr—Val—Xaa—Pro—Ala—Ala—Thr—Pro—Val—Gly—Gly—Gly—Gly—Gln— represented by SEQ ID NO. 4.

4. A polypeptide of claim 2 wherein said selected 23 kD polypeptide has an N-terminal amino acid sequence of:

NH$_2$—Ala—Thr—Ile—Thr—Val—Val—Asn—Lys—Phe—Ser—Tyr—Thr—Val—Xaa—Pro—Gly—Ala—Leu—Pro—Phe—Gly—Gly—Val—Gly—Leu—Gly—Pro—Gly—Gln— represented by SEQ ID NO.5.

5. A polypeptide of claim 2, wherein said selected 31 kD polypeptide is further characterized by an N-terminal amino acid sequence of:

NH$_2$—Ile—Gly—Val—Cys—Tyr—Gly—Val—Ile—Gly—Asn—Asn—Leu—Pro—Ser—Arg—Ser—Asp—Val—Val—Gln—Leu—Tyr—Arg—Ser—Gly—Xaa—Ile—Asn—Xaa—Met— represented by SEQ ID NO.6.

6. A polypeptide of claim 2, wherein said selected 33 kD polypeptide is further characterized by an N-terminal amino acid sequence of:

NH$_2$-Glu-Gln-Xaa-Gly-Ser-Gln-Ala-Gly-Gly-Ala-Thr-Xaa-Pro-Asn-Asn-Leu-Leurepresented by SEQ ID NO.7.

* * * * *

UNITED STATES PATENT AND TRADEMARK OFFICE
CERTIFICATE OF CORRECTION

PATENT NO. : 5,852,172

DATED : December 22, 1998

INVENTOR(S) : Griffith

It is certified that error appears in the above-identified patent and that said Letters Patent is hereby corrected as shown below:

Column 32, the listing in claim 2, column 2, line 2, "5.3" should read --8.3--; column 6, line 2, "5.8" should read --8.8--.

Column 33-34, cancel the underlining in claims 3-5 - used for indicating amendments in the claims.

Signed and Sealed this

Twenty-fourth Day of August, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,852,172
DATED : December 22, 1998
INVENTOR(S) : Griffith

It is certified that error appears in the above-identified patent and that said Letters Patent is hereby corrected as shown below:

<u>Title page,</u>
Item [63], Related U.S. Application Data, after "Continuation of Ser. No. 60,425, May 11, 1993 abandoned", insert --, which claimed priority from a PCT Filed Jun. 12, 1992, as PCT No. PCT/CA92/00255 --.

Signed and Sealed this

Sixteenth Day of July, 2002

*Attest:*

JAMES E. ROGAN
*Attesting Officer*   *Director of the United States Patent and Trademark Office*